(12) United States Patent
Levin et al.

(10) Patent No.: US 8,758,373 B2
(45) Date of Patent: Jun. 24, 2014

(54) MEANS AND METHOD FOR REVERSIBLY CONNECTING A PATCH TO A PATCH DEPLOYMENT DEVICE

(75) Inventors: Ofek Levin, Moshav Amirim (IL); Arie Levy, Ramat-Gan (IL)

(73) Assignee: Covidien LP, Mansfield, MA (US)

( * ) Notice: Subject to any disclaimer, the term of this patent is extended or adjusted under 35 U.S.C. 154(b) by 644 days.

(21) Appl. No.: 12/891,962

(22) Filed: Sep. 28, 2010

(65) Prior Publication Data
US 2011/0066166 A1 Mar. 17, 2011

Related U.S. Application Data

(60) Provisional application No. 61/302,186, filed on Feb. 8, 2010.

(51) Int. Cl.
*A61B 17/00* (2006.01)

(52) U.S. Cl.
USPC .......................... 606/151; 606/213

(58) Field of Classification Search
None
See application file for complete search history.

(56) References Cited

U.S. PATENT DOCUMENTS

| | | |
|---|---|---|
| 4,347,847 A | 9/1982 | Usher |
| 4,400,833 A | 8/1983 | Kurland |
| 4,452,245 A | 6/1984 | Usher |
| 4,485,816 A | 12/1984 | Krumme |
| 4,585,458 A | 4/1986 | Kurland |
| 4,633,873 A | 1/1987 | Dumican et al. |
| 4,838,884 A | 6/1989 | Dumican et al. |
| 4,930,674 A * | 6/1990 | Barak ..................... 227/179.1 |
| 5,019,096 A | 5/1991 | Fox, Jr. et al. |
| 5,116,357 A | 5/1992 | Eberbach |
| 5,122,155 A | 6/1992 | Eberbach |
| 5,125,553 A | 6/1992 | Oddsen et al. |
| 5,141,515 A | 8/1992 | Eberbach |
| 5,147,374 A | 9/1992 | Fernandez |
| 5,176,692 A | 1/1993 | Wilk et al. |
| 5,203,864 A | 4/1993 | Phillips |
| 5,219,077 A | 6/1993 | Transue |
| 5,249,682 A | 10/1993 | Transue |
| 5,258,000 A | 11/1993 | Gianturco |
| 5,263,969 A | 11/1993 | Phillips |
| 5,290,217 A | 3/1994 | Campos |
| 5,292,328 A | 3/1994 | Hain et al. |
| 5,304,187 A | 4/1994 | Green et al. |
| 5,333,624 A | 8/1994 | Tovey |
| 5,354,292 A | 10/1994 | Braeuer et al. |
| 5,364,002 A | 11/1994 | Green et al. |
| 5,364,004 A | 11/1994 | Davidson |

(Continued)

FOREIGN PATENT DOCUMENTS

| | | |
|---|---|---|
| CA | 2413904 A1 | 10/2003 |
| EP | 0328421 A2 | 8/1989 |

(Continued)

OTHER PUBLICATIONS

European Search Report for EP 11250797.5-2320 date of completion is Jun. 12, 2012 (9 pages).

(Continued)

*Primary Examiner* — Melanie Tyson
*Assistant Examiner* — Todd J Scherbel

(57) ABSTRACT

The present invention generally relates to devices and methods for reversibly coupling an implant to a deployment device.

18 Claims, 12 Drawing Sheets

(56) References Cited

U.S. PATENT DOCUMENTS

| | | | |
|---|---|---|---|
| 5,366,460 A | 11/1994 | Eberbach | |
| 5,368,602 A | 11/1994 | de la Torre | |
| 5,370,650 A | 12/1994 | Tovey et al. | |
| 5,376,097 A | 12/1994 | Phillips | |
| 5,383,477 A * | 1/1995 | DeMatteis | 128/898 |
| 5,397,331 A | 3/1995 | Himpens et al. | |
| 5,397,332 A * | 3/1995 | Kammerer et al. | 606/151 |
| 5,405,360 A | 4/1995 | Tovey | |
| 5,425,357 A | 6/1995 | Moll et al. | |
| 5,425,740 A | 6/1995 | Hutchinson | |
| 5,433,996 A | 7/1995 | Kranzler et al. | |
| 5,464,403 A | 11/1995 | Kieturakis et al. | |
| 5,497,933 A | 3/1996 | Defonzo et al. | |
| 5,560,224 A | 10/1996 | Tessler | |
| 5,560,532 A | 10/1996 | DeFonzo et al. | |
| 5,564,615 A | 10/1996 | Bishop et al. | |
| 5,569,273 A | 10/1996 | Titone et al. | |
| 5,577,654 A | 11/1996 | Bishop | |
| 5,588,580 A | 12/1996 | Paul et al. | |
| 5,588,581 A | 12/1996 | Conlon et al. | |
| 5,601,224 A | 2/1997 | Bishop et al. | |
| 5,614,284 A | 3/1997 | Kranzler et al. | |
| 5,626,587 A | 5/1997 | Bishop et al. | |
| 5,634,584 A | 6/1997 | Okorocha et al. | |
| 5,634,931 A | 6/1997 | Kugel | |
| 5,662,662 A | 9/1997 | Bishop et al. | |
| 5,695,525 A | 12/1997 | Mulhauser et al. | |
| 5,716,409 A | 2/1998 | Debbas | |
| 5,725,577 A | 3/1998 | Saxon | |
| 5,728,119 A | 3/1998 | Smith et al. | |
| 5,749,895 A | 5/1998 | Sawyer et al. | |
| 5,766,246 A | 6/1998 | Mulhauser et al. | |
| 5,769,864 A | 6/1998 | Kugel | |
| 5,779,728 A | 7/1998 | Lunsford et al. | |
| 5,814,058 A | 9/1998 | Carlson et al. | |
| 5,817,109 A | 10/1998 | McGarry et al. | |
| 5,824,082 A | 10/1998 | Brown | |
| 5,836,961 A | 11/1998 | Kieturakis et al. | |
| 5,854,383 A | 12/1998 | Erneta et al. | |
| 5,863,531 A | 1/1999 | Naughton et al. | |
| 5,911,726 A | 6/1999 | Belknap | |
| 5,916,225 A | 6/1999 | Kugel | |
| 5,925,058 A | 7/1999 | Smith et al. | |
| 5,951,997 A | 9/1999 | Bezwada et al. | |
| 5,954,767 A | 9/1999 | Pajotin et al. | |
| 5,972,007 A | 10/1999 | Sheffield et al. | |
| 5,972,008 A | 10/1999 | Kalinski et al. | |
| 5,990,378 A | 11/1999 | Ellis | |
| 6,004,333 A | 12/1999 | Sheffield et al. | |
| 6,066,776 A | 5/2000 | Goodwin et al. | |
| 6,090,116 A | 7/2000 | D'Aversa et al. | |
| 6,113,609 A | 9/2000 | Adams | |
| 6,113,624 A | 9/2000 | Bezwada et al. | |
| 6,166,286 A | 12/2000 | Trabucco | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,197,036 B1 | 3/2001 | Tripp et al. | |
| 6,214,020 B1 | 4/2001 | Mulhauser et al. | |
| 6,224,616 B1 | 5/2001 | Kugel | |
| 6,241,768 B1 | 6/2001 | Agarwal et al. | |
| 6,258,124 B1 | 7/2001 | Darois et al. | |
| 6,267,772 B1 | 7/2001 | Mulhauser et al. | |
| 6,280,453 B1 | 8/2001 | Kugel et al. | |
| 6,287,316 B1 | 9/2001 | Agarwal et al. | |
| 6,290,708 B1 | 9/2001 | Kugel et al. | |
| 6,312,442 B1 | 11/2001 | Kieturakis et al. | |
| 6,319,264 B1 | 11/2001 | Tormala et al. | |
| 6,368,541 B1 | 4/2002 | Pajotin et al. | |
| 6,383,201 B1 | 5/2002 | Dong | |
| 6,391,060 B1 | 5/2002 | Ory et al. | |
| 6,408,656 B1 | 6/2002 | Ory et al. | |
| 6,416,486 B1 | 7/2002 | Wampler | |
| 6,425,900 B1 | 7/2002 | Knodel et al. | |
| 6,425,924 B1 | 7/2002 | Rousseau | |
| 6,436,030 B2 | 8/2002 | Rehil | |
| 6,447,524 B1 | 9/2002 | Knodel et al. | |
| 6,478,803 B1 | 11/2002 | Kapec et al. | |
| 6,497,650 B1 | 12/2002 | Nicolo | |
| 6,517,584 B1 | 2/2003 | Lecalve | |
| 6,527,785 B2 | 3/2003 | Sancoff et al. | |
| 6,551,241 B1 | 4/2003 | Schultz | |
| 6,551,333 B2 | 4/2003 | Kuhns et al. | |
| 6,565,590 B2 | 5/2003 | Kieturakis et al. | |
| 6,575,988 B2 * | 6/2003 | Rousseau | 606/151 |
| 6,610,006 B1 | 8/2003 | Amid et al. | |
| 6,616,685 B2 | 9/2003 | Rousseau | |
| 6,638,208 B1 | 10/2003 | Natarajan et al. | |
| 6,638,284 B1 | 10/2003 | Rousseau et al. | |
| 6,652,595 B1 | 11/2003 | Nicolo | |
| 6,666,817 B2 | 12/2003 | Li | |
| 6,669,706 B2 | 12/2003 | Schmitt et al. | |
| 6,669,735 B1 | 12/2003 | Pelissier | |
| 6,676,643 B2 | 1/2004 | Brushey | |
| 6,689,047 B2 | 2/2004 | Gellman | |
| 6,736,823 B2 | 5/2004 | Darois et al. | |
| 6,736,854 B2 | 5/2004 | Vadurro et al. | |
| 6,737,371 B1 | 5/2004 | Planck et al. | |
| 6,746,458 B1 | 6/2004 | Cloud | |
| 6,755,867 B2 | 6/2004 | Rousseau | |
| 6,790,213 B2 | 9/2004 | Cherok et al. | |
| 6,800,082 B2 | 10/2004 | Rousseau | |
| 6,805,669 B2 | 10/2004 | Swanbom | |
| 6,833,408 B2 | 12/2004 | Sehl et al. | |
| 6,893,452 B2 | 5/2005 | Jacobs | |
| 6,936,052 B2 | 8/2005 | Gellman et al. | |
| 6,953,428 B2 | 10/2005 | Gellman et al. | |
| 6,960,233 B1 | 11/2005 | Berg et al. | |
| 6,966,916 B2 | 11/2005 | Kumar | |
| 6,974,586 B2 | 12/2005 | Greenhalgh et al. | |
| 6,991,597 B2 | 1/2006 | Gellman et al. | |
| 7,001,405 B2 | 2/2006 | Kieturakis et al. | |
| 7,011,688 B2 | 3/2006 | Gryska et al. | |
| 7,025,772 B2 | 4/2006 | Gellman et al. | |
| 7,049,345 B2 | 5/2006 | Holmes-Farley | |
| 7,094,261 B2 | 8/2006 | Zotti et al. | |
| 7,119,062 B1 | 10/2006 | Alvis et al. | |
| 7,148,315 B2 | 12/2006 | Erneta et al. | |
| 7,198,046 B1 | 4/2007 | Argenta et al. | |
| 7,214,236 B2 | 5/2007 | Kieturakis et al. | |
| 7,216,651 B2 | 5/2007 | Argenta et al. | |
| 7,220,282 B2 | 5/2007 | Kuslich | |
| 7,229,452 B2 | 6/2007 | Kayan | |
| 7,235,043 B2 | 6/2007 | Gellman et al. | |
| 7,235,295 B2 | 6/2007 | Laurencin et al. | |
| 7,331,199 B2 | 2/2008 | Ory et al. | |
| 7,381,225 B2 | 6/2008 | Croce et al. | |
| 7,404,819 B1 | 7/2008 | Darios et al. | |
| 7,406,969 B2 | 8/2008 | Duchon et al. | |
| 7,407,480 B2 | 8/2008 | Staskin et al. | |
| 7,491,232 B2 | 2/2009 | Bolduc et al. | |
| 7,500,945 B2 | 3/2009 | Cox et al. | |
| 7,500,993 B2 | 3/2009 | De La Torre et al. | |
| 7,544,213 B2 | 6/2009 | Adams | |
| 7,553,329 B2 | 6/2009 | Lambrecht et al. | |
| 7,553,330 B2 | 6/2009 | Lambrecht et al. | |
| RE40,833 E | 7/2009 | Wintermantel et al. | |
| 7,566,337 B2 | 7/2009 | Sogaard-Andersen et al. | |
| 7,594,921 B2 | 9/2009 | Browning | |
| 7,601,118 B2 | 10/2009 | Smith et al. | |
| 7,819,797 B2 * | 10/2010 | Vanden Hoek et al. | 600/37 |
| 8,097,008 B2 * | 1/2012 | Henderson | 606/151 |
| 2001/0016754 A1 | 8/2001 | Adams et al. | |
| 2001/0018592 A1 | 8/2001 | Schaller et al. | |
| 2001/0018593 A1 | 8/2001 | Nguyen et al. | |
| 2001/0027347 A1 | 10/2001 | Rousseau | |
| 2001/0044637 A1 | 11/2001 | Jacobs et al. | |
| 2001/0049538 A1 | 12/2001 | Trabucco | |
| 2001/0049539 A1 | 12/2001 | Rehil | |
| 2001/0053919 A1 | 12/2001 | Kieturakis et al. | |
| 2001/0056275 A1 | 12/2001 | Brushey | |
| 2002/0010457 A1 | 1/2002 | Duchon et al. | |
| 2002/0010480 A1 | 1/2002 | Sancoff et al. | |
| 2002/0010490 A1 | 1/2002 | Schaller et al. | |

(56) References Cited

U.S. PATENT DOCUMENTS

| | | |
|---|---|---|
| 2002/0010494 A1 | 1/2002 | Policker et al. |
| 2002/0042658 A1 | 4/2002 | Tyagi |
| 2002/0049503 A1 | 4/2002 | Milbocker |
| 2002/0049504 A1 | 4/2002 | Barault |
| 2002/0052612 A1 | 5/2002 | Schmitt et al. |
| 2002/0052654 A1 | 5/2002 | Darois et al. |
| 2002/0058967 A1 | 5/2002 | Jervis |
| 2002/0066360 A1 | 6/2002 | Greenhalgh et al. |
| 2002/0077652 A1 | 6/2002 | Kieturakis et al. |
| 2002/0082621 A1 | 6/2002 | Schurr et al. |
| 2002/0087170 A1 | 7/2002 | Kuhns et al. |
| 2002/0091405 A1 | 7/2002 | Kieturakis et al. |
| 2002/0103434 A1 | 8/2002 | Swanbom |
| 2002/0103494 A1 | 8/2002 | Pacey |
| 2002/0107539 A1 | 8/2002 | Kieturakis et al. |
| 2002/0116070 A1 | 8/2002 | Amara et al. |
| 2002/0117534 A1 | 8/2002 | Green et al. |
| 2002/0147457 A1 | 10/2002 | Rousseau |
| 2002/0165561 A1 | 11/2002 | Ainsworth et al. |
| 2002/0169452 A1 | 11/2002 | Tormala et al. |
| 2002/0173803 A1 | 11/2002 | Ainsworth et al. |
| 2002/0173804 A1 | 11/2002 | Rousseau |
| 2002/0183765 A1 | 12/2002 | Adams |
| 2002/0183768 A1 | 12/2002 | Deem et al. |
| 2002/0188317 A1 | 12/2002 | Rousseau |
| 2003/0004581 A1 | 1/2003 | Rousseau |
| 2003/0039626 A1 | 2/2003 | Holmes-Farley |
| 2003/0065359 A1 | 4/2003 | Weller et al. |
| 2003/0073976 A1 | 4/2003 | Brushey |
| 2003/0078602 A1 | 4/2003 | Rousseau |
| 2003/0078603 A1 | 4/2003 | Schaller et al. |
| 2003/0109892 A1 | 6/2003 | Deem et al. |
| 2003/0119985 A1 | 6/2003 | Sehl et al. |
| 2003/0120265 A1 | 6/2003 | Deem et al. |
| 2003/0120299 A1 | 6/2003 | Kieturakis et al. |
| 2003/0130745 A1 | 7/2003 | Cherok et al. |
| 2003/0166628 A1 | 9/2003 | Doyle et al. |
| 2003/0171761 A1 | 9/2003 | Sancoff et al. |
| 2003/0171812 A1 | 9/2003 | Grunberg et al. |
| 2003/0171823 A1 | 9/2003 | Zotti et al. |
| 2003/0187516 A1 | 10/2003 | Amid et al. |
| 2003/0195531 A1 | 10/2003 | Gardiner et al. |
| 2003/0208211 A1 | 11/2003 | Kortenbach |
| 2003/0212460 A1 | 11/2003 | Darois et al. |
| 2003/0212461 A1 | 11/2003 | Vadurro et al. |
| 2003/0212462 A1 | 11/2003 | Gryska et al. |
| 2003/0220660 A1 | 11/2003 | Kortenbach et al. |
| 2003/0225355 A1 | 12/2003 | Butler |
| 2003/0225420 A1 | 12/2003 | Wardle |
| 2004/0002679 A1 | 1/2004 | Trout et al. |
| 2004/0024386 A1 | 2/2004 | Deem et al. |
| 2004/0030217 A1 | 2/2004 | Yeung et al. |
| 2004/0039453 A1 | 2/2004 | Anderson et al. |
| 2004/0049227 A1 | 3/2004 | Jervis |
| 2004/0054376 A1 | 3/2004 | Ory et al. |
| 2004/0059356 A1 | 3/2004 | Gringas |
| 2004/0064131 A1 | 4/2004 | Brushey |
| 2004/0073257 A1 | 4/2004 | Spitz |
| 2004/0082755 A1 | 4/2004 | Erneta et al. |
| 2004/0087970 A1 | 5/2004 | Chu et al. |
| 2004/0087979 A1 | 5/2004 | Field et al. |
| 2004/0087980 A1 | 5/2004 | Ford et al. |
| 2004/0092937 A1 | 5/2004 | Criscuolo et al. |
| 2004/0092969 A1 | 5/2004 | Kumar |
| 2004/0092970 A1 | 5/2004 | Xavier |
| 2004/0097986 A1 | 5/2004 | Adams |
| 2004/0122452 A1 | 6/2004 | Deem et al. |
| 2004/0144395 A1 | 7/2004 | Evans et al. |
| 2004/0152977 A1 | 8/2004 | Duchon et al. |
| 2004/0152978 A1 | 8/2004 | Duchon et al. |
| 2004/0172048 A1 | 9/2004 | Browning |
| 2004/0181288 A1 | 9/2004 | Darois et al. |
| 2004/0193043 A1 | 9/2004 | Duchon et al. |
| 2004/0215219 A1 | 10/2004 | Eldridge et al. |
| 2004/0225247 A1 | 11/2004 | Pugsley et al. |
| 2004/0225373 A1 | 11/2004 | Pugsley et al. |
| 2004/0230208 A1 | 11/2004 | Shayani |
| 2004/0234576 A1 | 11/2004 | Martin et al. |
| 2004/0249412 A1 | 12/2004 | Snow et al. |
| 2004/0254592 A1 | 12/2004 | DiCarlo et al. |
| 2005/0004427 A1 | 1/2005 | Cervigni |
| 2005/0010239 A1 | 1/2005 | Chefitz |
| 2005/0015102 A1 | 1/2005 | Chefitz |
| 2005/0019436 A1 | 1/2005 | Burch et al. |
| 2005/0021058 A1 | 1/2005 | Negro |
| 2005/0027369 A1 | 2/2005 | Eldridge et al. |
| 2005/0038452 A1 | 2/2005 | Chu |
| 2005/0054771 A1 | 3/2005 | Sehl et al. |
| 2005/0060038 A1 | 3/2005 | Lambrecht et al. |
| 2005/0065072 A1 | 3/2005 | Keeler et al. |
| 2005/0113849 A1 | 5/2005 | Popadiuk et al. |
| 2005/0113858 A1 | 5/2005 | Deutsch |
| 2005/0118239 A1 | 6/2005 | Sabesan |
| 2005/0129733 A1 | 6/2005 | Milbocker et al. |
| 2005/0154361 A1 | 7/2005 | Sabesan |
| 2005/0159777 A1 | 7/2005 | Spitz |
| 2005/0165425 A1 | 7/2005 | Croce et al. |
| 2005/0169959 A1 | 8/2005 | Hunter et al. |
| 2005/0177225 A1 | 8/2005 | Hunter et al. |
| 2005/0192600 A1 | 9/2005 | Nicolo et al. |
| 2005/0202067 A1 | 9/2005 | Lendlein et al. |
| 2005/0228408 A1 | 10/2005 | Fricke et al. |
| 2005/0234557 A1 | 10/2005 | Lambrecht et al. |
| 2005/0240269 A1 | 10/2005 | Lambrecht et al. |
| 2005/0244455 A1 | 11/2005 | Greenawalt |
| 2005/0245787 A1 | 11/2005 | Cox et al. |
| 2005/0249770 A1 | 11/2005 | Hunter |
| 2005/0256532 A1* | 11/2005 | Nayak et al. .................. 606/151 |
| 2005/0267325 A1 | 12/2005 | Bouchier et al. |
| 2005/0283246 A1 | 12/2005 | Cauthen et al. |
| 2005/0283962 A1 | 12/2005 | Boudjemline |
| 2005/0288691 A1 | 12/2005 | Leiboff |
| 2005/0288775 A1 | 12/2005 | Dong |
| 2006/0009802 A1 | 1/2006 | Modesitt |
| 2006/0015142 A1 | 1/2006 | Malazgirt |
| 2006/0015143 A1 | 1/2006 | Alvarado |
| 2006/0024238 A1 | 2/2006 | Barth et al. |
| 2006/0025649 A1 | 2/2006 | Smith et al. |
| 2006/0039896 A1 | 2/2006 | Kleinsek et al. |
| 2006/0052816 A1 | 3/2006 | Bates et al. |
| 2006/0079558 A1 | 4/2006 | Aberg et al. |
| 2006/0079559 A1 | 4/2006 | Aberg et al. |
| 2006/0083710 A1 | 4/2006 | Joerger et al. |
| 2006/0105026 A1 | 5/2006 | Fortune et al. |
| 2006/0116696 A1 | 6/2006 | Odermatt et al. |
| 2006/0122637 A1 | 6/2006 | Barker |
| 2006/0127353 A1 | 6/2006 | Holmes-Farley |
| 2006/0129152 A1 | 6/2006 | Shipp |
| 2006/0129154 A1 | 6/2006 | Shipp |
| 2006/0147488 A1 | 7/2006 | Wohlert |
| 2006/0155165 A1 | 7/2006 | Vanden Hoek et al. |
| 2006/0155379 A1 | 7/2006 | Heneveld et al. |
| 2006/0177489 A1 | 8/2006 | Massouda et al. |
| 2006/0189918 A1 | 8/2006 | Barker |
| 2006/0206118 A1 | 9/2006 | Kim et al. |
| 2006/0206178 A1 | 9/2006 | Kim |
| 2006/0210602 A1 | 9/2006 | Sehl et al. |
| 2006/0217812 A1 | 9/2006 | Lambrecht et al. |
| 2006/0228391 A1 | 10/2006 | Seyedin et al. |
| 2006/0233852 A1 | 10/2006 | Milbocker |
| 2006/0240063 A9 | 10/2006 | Hunter et al. |
| 2006/0251702 A1 | 11/2006 | Janis et al. |
| 2006/0253203 A1 | 11/2006 | Alvarado |
| 2006/0282103 A1 | 12/2006 | Fricke et al. |
| 2006/0282105 A1 | 12/2006 | Ford et al. |
| 2006/0287729 A1 | 12/2006 | Segal et al. |
| 2006/0287730 A1 | 12/2006 | Segal et al. |
| 2007/0016300 A1 | 1/2007 | Kuslich |
| 2007/0026043 A1 | 2/2007 | Guan et al. |
| 2007/0027358 A1 | 2/2007 | Gertner et al. |
| 2007/0032881 A1 | 2/2007 | Browning |
| 2007/0036876 A1 | 2/2007 | Burch et al. |
| 2007/0038220 A1 | 2/2007 | Shipp |
| 2007/0100355 A1 | 5/2007 | Bonde et al. |

(56) References Cited

U.S. PATENT DOCUMENTS

| | | |
|---|---|---|
| 2007/0110786 A1 | 5/2007 | Tenney et al. |
| 2007/0111937 A1 | 5/2007 | Pickar et al. |
| 2007/0118133 A1 | 5/2007 | Lambrecht et al. |
| 2007/0122425 A1 | 5/2007 | Keeler et al. |
| 2007/0134292 A1 | 6/2007 | Suokas et al. |
| 2007/0135929 A1 | 6/2007 | Williams et al. |
| 2007/0156245 A1 | 7/2007 | Cauthen et al. |
| 2007/0162030 A1 | 7/2007 | Aranyi et al. |
| 2007/0162135 A1 | 7/2007 | Segal et al. |
| 2007/0173864 A1 | 7/2007 | Chu |
| 2007/0173888 A1 | 7/2007 | Gertner et al. |
| 2007/0179335 A1 | 8/2007 | Gertner et al. |
| 2007/0184277 A1 | 8/2007 | Schussler et al. |
| 2007/0185506 A1* | 8/2007 | Jackson .................. 606/151 |
| 2007/0185541 A1 | 8/2007 | DiUbaldi et al. |
| 2007/0202173 A1 | 8/2007 | Cueto-Garcia |
| 2007/0203507 A1 | 8/2007 | McLaughlin et al. |
| 2007/0207186 A1 | 9/2007 | Scanlon et al. |
| 2007/0208358 A1 | 9/2007 | Kayan |
| 2007/0219569 A1 | 9/2007 | Shayani |
| 2007/0225791 A1 | 9/2007 | Molitor et al. |
| 2007/0244502 A1 | 10/2007 | Deutsch |
| 2007/0250087 A1* | 10/2007 | Makower et al. .......... 606/157 |
| 2007/0250147 A1 | 10/2007 | Walther et al. |
| 2007/0260179 A1 | 11/2007 | Sholev et al. |
| 2007/0260268 A1 | 11/2007 | Bartee et al. |
| 2007/0265710 A1 | 11/2007 | Brown et al. |
| 2007/0270752 A1 | 11/2007 | LaBombard |
| 2007/0280990 A1 | 12/2007 | Stopek |
| 2007/0293717 A1 | 12/2007 | Kaleta et al. |
| 2007/0293878 A1 | 12/2007 | Butsch |
| 2007/0299300 A1 | 12/2007 | Smith et al. |
| 2007/0299542 A1 | 12/2007 | Mathisen et al. |
| 2008/0015501 A1 | 1/2008 | Gertner |
| 2008/0021545 A1 | 1/2008 | Reneker et al. |
| 2008/0033461 A1 | 2/2008 | Koeckerling et al. |
| 2008/0035243 A1 | 2/2008 | Breitenkamp et al. |
| 2008/0045952 A1 | 2/2008 | Kuslich |
| 2008/0065229 A1 | 3/2008 | Adams |
| 2008/0086216 A1 | 4/2008 | Wilson et al. |
| 2008/0091222 A1 | 4/2008 | Deusch et al. |
| 2008/0091276 A1 | 4/2008 | Deusch et al. |
| 2008/0103351 A1 | 5/2008 | Montpetit et al. |
| 2008/0113035 A1 | 5/2008 | Hunter |
| 2008/0125869 A1 | 5/2008 | Paz et al. |
| 2008/0131509 A1 | 6/2008 | Hossainy et al. |
| 2008/0132602 A1 | 6/2008 | Rizk et al. |
| 2008/0147198 A1 | 6/2008 | Cherok et al. |
| 2008/0147200 A1 | 6/2008 | Rousseau et al. |
| 2008/0167519 A1 | 7/2008 | St-Germain |
| 2008/0167667 A1 | 7/2008 | Criscuolo et al. |
| 2008/0167668 A1 | 7/2008 | Criscuolo et al. |
| 2008/0188874 A1* | 8/2008 | Henderson ................ 606/151 |
| 2008/0193494 A1 | 8/2008 | Sabesan |
| 2008/0195121 A1 | 8/2008 | Eldar et al. |
| 2008/0200979 A1 | 8/2008 | Dieck et al. |
| 2008/0215154 A1 | 9/2008 | Lambrecht et al. |
| 2008/0243149 A1 | 10/2008 | Kockerling et al. |
| 2008/0255593 A1 | 10/2008 | St-Germain |
| 2008/0260794 A1 | 10/2008 | Lauritzen et al. |
| 2008/0269896 A1 | 10/2008 | Cherok et al. |
| 2008/0281433 A1 | 11/2008 | Chang et al. |
| 2008/0287970 A1 | 11/2008 | Amato et al. |
| 2008/0306497 A1 | 12/2008 | Brown et al. |
| 2008/0312751 A1 | 12/2008 | Pugsley et al. |
| 2009/0004239 A1 | 1/2009 | Ladet et al. |
| 2009/0005867 A1 | 1/2009 | Lefranc et al. |
| 2009/0012350 A1 | 1/2009 | Tihon |
| 2009/0012546 A1 | 1/2009 | N'diaye et al. |
| 2009/0018559 A1 | 1/2009 | Buevich et al. |
| 2009/0030434 A1 | 1/2009 | Paz et al. |
| 2009/0030522 A1 | 1/2009 | Cauthen, III et al. |
| 2009/0030527 A1 | 1/2009 | Richter |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0036996 A1 | 2/2009 | Roeber |
| 2009/0062823 A1 | 3/2009 | Richter |
| 2009/0069826 A1 | 3/2009 | Walther et al. |
| 2009/0105526 A1 | 4/2009 | Pirolli Torelli et al. |
| 2009/0125041 A1 | 5/2009 | Dudai |
| 2009/0137864 A1 | 5/2009 | Cox et al. |
| 2009/0149875 A1 | 6/2009 | Abele et al. |
| 2009/0155332 A1 | 6/2009 | Sherry et al. |
| 2009/0157184 A1 | 6/2009 | Cauthen, III et al. |
| 2009/0157195 A1 | 6/2009 | Siedle |
| 2009/0162273 A1 | 6/2009 | Lawrynowicz et al. |
| 2009/0182190 A1 | 7/2009 | Dann |
| 2009/0182352 A1 | 7/2009 | Paz et al. |
| 2009/0187258 A1 | 7/2009 | Ip et al. |
| 2009/0192346 A1 | 7/2009 | Rosenblatt |
| 2009/0192528 A1 | 7/2009 | Higgins et al. |
| 2009/0198260 A1 | 8/2009 | Ford et al. |
| 2009/0204130 A1 | 8/2009 | Kantsevoy et al. |
| 2009/0204227 A1 | 8/2009 | Derwin et al. |
| 2009/0216075 A1 | 8/2009 | Bell et al. |
| 2009/0216104 A1 | 8/2009 | DeSimone et al. |
| 2009/0216338 A1 | 8/2009 | Gringas et al. |
| 2009/0234379 A1 | 9/2009 | Rehnke |
| 2009/0234461 A1 | 9/2009 | Rehnke |
| 2009/0240342 A1 | 9/2009 | Lindh et al. |
| 2009/0240343 A1 | 9/2009 | Adams |
| 2009/0248048 A1 | 10/2009 | Milbocker |
| 2009/0254103 A1 | 10/2009 | Deutsch |
| 2009/0259094 A1 | 10/2009 | Bouchier et al. |
| 2009/0281563 A1 | 11/2009 | Newell et al. |
| 2010/0069930 A1 | 3/2010 | Roslin et al. |
| 2010/0312357 A1* | 12/2010 | Levin et al. ............. 623/23.72 |
| 2010/0318121 A1* | 12/2010 | Levin et al. .............. 606/213 |
| 2011/0004221 A1 | 1/2011 | Euteneuer et al. |
| 2011/0040310 A1* | 2/2011 | Levin et al. .............. 606/151 |
| 2011/0040311 A1* | 2/2011 | Levin et al. .............. 606/151 |
| 2011/0054500 A1* | 3/2011 | Levin et al. .............. 606/151 |
| 2012/0259347 A1* | 10/2012 | Abuzaina et al. .......... 606/142 |
| 2013/0190784 A1* | 7/2013 | Palmer et al. ............ 606/151 |

FOREIGN PATENT DOCUMENTS

| | | |
|---|---|---|
| EP | 0525791 A1 | 2/1993 |
| EP | 0537769 A1 | 4/1993 |
| EP | 0556018 A1 | 8/1993 |
| EP | 0557963 A1 | 9/1993 |
| EP | 0557964 A1 | 9/1993 |
| EP | 0573273 A2 | 12/1993 |
| EP | 0579377 A2 | 1/1994 |
| EP | 0581036 A1 | 2/1994 |
| EP | 0614650 A2 | 9/1994 |
| EP | 0702934 A1 | 3/1996 |
| EP | 0744162 A2 | 11/1996 |
| EP | 0581036 | 1/1997 |
| EP | 0519022 B1 | 12/1997 |
| EP | 0827724 A2 | 3/1998 |
| EP | 0553344 B1 | 9/1998 |
| EP | 0746258 B1 | 9/1998 |
| EP | 0898944 A2 | 3/1999 |
| EP | 0986993 A1 | 3/2000 |
| EP | 0837660 B1 | 5/2000 |
| EP | 1060714 A2 | 12/2000 |
| EP | 1145693 A2 | 10/2001 |
| EP | 1181899 A2 | 2/2002 |
| EP | 1219265 A2 | 7/2002 |
| EP | 0746267 B1 | 11/2002 |
| EP | 1018980 B1 | 1/2003 |
| EP | 1306061 A2 | 5/2003 |
| EP | 1317904 A1 | 6/2003 |
| EP | 0783270 B1 | 6/2004 |
| EP | 1200010 B1 | 3/2005 |
| EP | 1164967 B1 | 5/2005 |
| EP | 1541183 A1 | 6/2005 |
| EP | WO2005082273 A1 | 9/2005 |
| EP | 0828453 B1 | 11/2005 |
| EP | 1001717 B1 | 11/2005 |
| EP | 1303230 B1 | 11/2005 |
| EP | 1404250 B1 | 2/2006 |

(56) References Cited

FOREIGN PATENT DOCUMENTS

| | | |
|---|---|---|
| EP | 1674048 A1 | 6/2006 |
| EP | 1274473 B1 | 7/2006 |
| EP | 0934024 B1 | 8/2006 |
| EP | 1700579 A1 | 9/2006 |
| EP | 1704832 A2 | 9/2006 |
| EP | 200614650 A2 | 10/2006 |
| EP | 1079741 B1 | 11/2006 |
| EP | 0964645 B1 | 7/2007 |
| EP | 1163019 B1 | 10/2007 |
| EP | 1849440 A1 | 10/2007 |
| EP | 1867348 A2 | 12/2007 |
| EP | 1870056 A1 | 12/2007 |
| EP | 1531739 B1 | 2/2008 |
| EP | 1406557 B1 | 11/2008 |
| EP | 1990014 A2 | 11/2008 |
| EP | 2002800 A1 | 12/2008 |
| EP | 1505927 B1 | 1/2009 |
| EP | 1372525 B1 | 3/2009 |
| EP | 1653880 B1 | 4/2009 |
| EP | 2050474 A2 | 4/2009 |
| EP | 1940312 B1 | 7/2009 |
| FR | 2789888 | 8/2000 |
| WO | WO8204390 A1 | 12/1982 |
| WO | WO92/06639 | 4/1992 |
| WO | WO9206639 A2 | 4/1992 |
| WO | WO9211824 A1 | 7/1992 |
| WO | WO9219162 A2 | 11/1992 |
| WO | WO9221293 A1 | 12/1992 |
| WO | WO9303685 A1 | 3/1993 |
| WO | WO9309722 A1 | 5/1993 |
| WO | WO9317635 A1 | 9/1993 |
| WO | WO9417747 A1 | 8/1994 |
| WO | WO9419029 A1 | 9/1994 |
| WO | WO94/27535 | 12/1994 |
| WO | WO9427535 A1 | 12/1994 |
| WO | WO9530374 A1 | 11/1995 |
| WO | WO9531140 A1 | 11/1995 |
| WO | WO9603091 A1 | 2/1996 |
| WO | WO9603165 A1 | 2/1996 |
| WO | WO9606634 A1 | 3/1996 |
| WO | WO9609795 A1 | 4/1996 |
| WO | WO9640307 A1 | 12/1996 |
| WO | WO9702789 A1 | 1/1997 |
| WO | WO9722371 A1 | 6/1997 |
| WO | WO9732526 A1 | 9/1997 |
| WO | WO9735533 A1 | 10/1997 |
| WO | WO9803713 A1 | 1/1998 |
| WO | WO9811814 | 3/1998 |
| WO | WO9814134 A2 | 4/1998 |
| WO | WO9816153 A1 | 4/1998 |
| WO | WO9903422 A1 | 1/1999 |
| WO | WO9905992 A1 | 2/1999 |
| WO | WO9916381 A1 | 4/1999 |
| WO | WO9951163 A1 | 10/1999 |
| WO | WO9960931 A1 | 12/1999 |
| WO | WO9962406 A2 | 12/1999 |
| WO | WO9963051 A2 | 12/1999 |
| WO | WO0007520 A1 | 2/2000 |
| WO | WO0016822 A2 | 3/2000 |
| WO | WO0056376 A1 | 9/2000 |
| WO | WO0057812 A1 | 10/2000 |
| WO | WO0067663 A1 | 11/2000 |
| WO | WO0108594 A1 | 2/2001 |
| WO | WO0126588 A2 | 4/2001 |
| WO | WO0154589 A1 | 8/2001 |
| WO | WO0170322 A1 | 9/2001 |
| WO | WO0180788 A2 | 11/2001 |
| WO | WO0185058 A2 | 11/2001 |
| WO | WO0185060 | 11/2001 |
| WO | WO0189390 A1 | 11/2001 |
| WO | WO0189392 A2 | 11/2001 |
| WO | WO0207648 A1 | 1/2002 |
| WO | WO0222047 A1 | 3/2002 |
| WO | WO02024080 A2 | 3/2002 |
| WO | WO0232346 A1 | 4/2002 |
| WO | WO0234140 A2 | 5/2002 |
| WO | WO0235990 A2 | 5/2002 |
| WO | WO02078568 A1 | 10/2002 |
| WO | WO02080779 A1 | 10/2002 |
| WO | WO02080780 A1 | 10/2002 |
| WO | WO02/091953 | 11/2002 |
| WO | WO02087425 A2 | 11/2002 |
| WO | WO02091928 A1 | 11/2002 |
| WO | WO02091953 A1 | 11/2002 |
| WO | WO02096327 A2 | 12/2002 |
| WO | WO03002029 A1 | 1/2003 |
| WO | WO03032867 A1 | 4/2003 |
| WO | WO03059201 A1 | 7/2003 |
| WO | WO03059217 A1 | 7/2003 |
| WO | WO03077730 A2 | 9/2003 |
| WO | WO03082125 A1 | 10/2003 |
| WO | WO03084410 A1 | 10/2003 |
| WO | WO03090633 A2 | 11/2003 |
| WO | WO03094781 A1 | 11/2003 |
| WO | WO03094783 A1 | 11/2003 |
| WO | WO03094786 A1 | 11/2003 |
| WO | WO03094787 A1 | 11/2003 |
| WO | WO03096909 A1 | 11/2003 |
| WO | WO03096929 A1 | 11/2003 |
| WO | WO03097011 A1 | 11/2003 |
| WO | WO03099160 A1 | 12/2003 |
| WO | WO2004004600 A1 | 1/2004 |
| WO | WO2004006808 A2 | 1/2004 |
| WO | WO200412579 A2 | 2/2004 |
| WO | WO2004012627 A1 | 2/2004 |
| WO | WO2004024030 A1 | 3/2004 |
| WO | WO2004037123 A1 | 5/2004 |
| WO | WO2004/062529 | 7/2004 |
| WO | WO2004060425 A2 | 7/2004 |
| WO | WO2004062529 A2 | 7/2004 |
| WO | WO2004062530 A1 | 7/2004 |
| WO | WO2004028547 A1 | 8/2004 |
| WO | WO2004069866 A1 | 8/2004 |
| WO | WO2004/080348 | 9/2004 |
| WO | WO2004080348 A1 | 9/2004 |
| WO | WO2004087227 A1 | 10/2004 |
| WO | WO2004093737 A1 | 11/2004 |
| WO | WO2004098461 A2 | 11/2004 |
| WO | WO2004098665 A1 | 11/2004 |
| WO | WO2004101002 A2 | 11/2004 |
| WO | WO2004103166 A2 | 12/2004 |
| WO | WO2004103414 A2 | 12/2004 |
| WO | WO2005003351 A1 | 1/2005 |
| WO | WO2005007209 A1 | 1/2005 |
| WO | WO2005014634 A1 | 2/2005 |
| WO | WO2005018494 A1 | 3/2005 |
| WO | WO2005019315 A1 | 3/2005 |
| WO | WO2005035548 A1 | 4/2005 |
| WO | WO2005044143 A1 | 5/2005 |
| WO | WO2005051172 A2 | 6/2005 |
| WO | WO2005055958 A2 | 6/2005 |
| WO | WO2005065324 A1 | 7/2005 |
| WO | WO2005079335 A2 | 9/2005 |
| WO | WO2005082274 A1 | 9/2005 |
| WO | WO2005094721 A1 | 10/2005 |
| WO | WO2005102209 A1 | 11/2005 |
| WO | WO2005105172 A1 | 11/2005 |
| WO | WO2005110243 A2 | 11/2005 |
| WO | WO2005110273 A1 | 11/2005 |
| WO | WO2006002439 A1 | 1/2006 |
| WO | WO2006008429 A1 | 1/2006 |
| WO | WO2006012353 A2 | 2/2006 |
| WO | WO2006013337 A2 | 2/2006 |
| WO | WO2006015031 A2 | 2/2006 |
| WO | WO2006034117 A1 | 3/2006 |
| WO | WO2006036936 A2 | 4/2006 |
| WO | WO2006037047 A2 | 4/2006 |
| WO | WO2006040760 A2 | 4/2006 |
| WO | WO2006047645 A2 | 5/2006 |
| WO | WO2006048885 A1 | 5/2006 |
| WO | WO2006082587 A2 | 8/2006 |
| WO | WO2006086339 A2 | 8/2006 |
| WO | WO2006092159 A1 | 9/2006 |
| WO | WO2006092236 A1 | 9/2006 |

(56) References Cited

FOREIGN PATENT DOCUMENTS

| | | |
|---|---|---|
| WO | WO2006102457 A2 | 9/2006 |
| WO | W2006116000 A2 | 11/2006 |
| WO | WO2006119034 A2 | 11/2006 |
| WO | WO2007021759 A2 | 2/2007 |
| WO | WO2007021834 A1 | 2/2007 |
| WO | WO2007/025302 | 3/2007 |
| WO | WO2007/030676 | 3/2007 |
| WO | WO2007025293 A2 | 3/2007 |
| WO | WO2007025296 A2 | 3/2007 |
| WO | WO2007025302 A2 | 3/2007 |
| WO | WO2007030676 A2 | 3/2007 |
| WO | WO2007034145 A2 | 3/2007 |
| WO | WO2007050382 A1 | 5/2007 |
| WO | WO2007051221 A1 | 5/2007 |
| WO | WO2007055755 A1 | 5/2007 |
| WO | WO2007070141 A1 | 6/2007 |
| WO | WO2007072469 A2 | 6/2007 |
| WO | WO2007081955 A1 | 7/2007 |
| WO | WO2007087132 A1 | 8/2007 |
| WO | WO2007115110 A2 | 10/2007 |
| WO | WO2007129220 A2 | 11/2007 |
| WO | WO2007133311 A2 | 11/2007 |
| WO | WO2007136820 A2 | 11/2007 |
| WO | WO2007137211 A2 | 11/2007 |
| WO | WO2007143726 A2 | 12/2007 |
| WO | WO2007144782 A2 | 12/2007 |
| WO | WO2007146784 A2 | 12/2007 |
| WO | WO2008006097 A2 | 1/2008 |
| WO | WO2008026905 A2 | 3/2008 |
| WO | WO2008030873 A2 | 3/2008 |
| WO | WO2008030939 A2 | 3/2008 |
| WO | WO2008/045635 | 4/2008 |
| WO | WO2008045635 A2 | 4/2008 |
| WO | WO2008055028 A1 | 5/2008 |
| WO | WO2008/065653 | 6/2008 |
| WO | WO2008065653 A1 | 6/2008 |
| WO | WO2008069919 A2 | 6/2008 |
| WO | WO2008083484 A1 | 7/2008 |
| WO | WO2008085825 A1 | 7/2008 |
| WO | WO2008/099382 | 8/2008 |
| WO | WO2008094217 A1 | 8/2008 |
| WO | WO2008094842 A1 | 8/2008 |
| WO | WO2008099382 A1 | 8/2008 |
| WO | WO2008112437 A2 | 9/2008 |
| WO | WO2008124056 A1 | 10/2008 |
| WO | WO2008140989 A2 | 11/2008 |
| WO | WO2008157497 A2 | 12/2008 |
| WO | WO2008157777 A1 | 12/2008 |
| WO | WO2009005625 A1 | 1/2009 |
| WO | WO2009005634 A1 | 1/2009 |
| WO | WO2009011824 A1 | 1/2009 |
| WO | WO2009012001 A1 | 1/2009 |
| WO | WO2009022348 A1 | 2/2009 |
| WO | WO2009036094 A2 | 3/2009 |
| WO | WO2009039371 A1 | 3/2009 |
| WO | WO2009/050717 | 4/2009 |
| WO | WO2009042442 A1 | 4/2009 |
| WO | WO2009048314 A1 | 4/2009 |
| WO | WO2009050717 A2 | 4/2009 |
| WO | WO2009059005 A1 | 5/2009 |
| WO | WO2009064845 A2 | 5/2009 |
| WO | WO2009069119 A1 | 6/2009 |
| WO | WO2009075786 A1 | 6/2009 |
| WO | WO2009075932 A1 | 6/2009 |
| WO | WO2009075933 A1 | 6/2009 |
| WO | WO2009086446 A1 | 7/2009 |
| WO | WO2009092294 A1 | 7/2009 |
| WO | WO2009094015 A1 | 7/2009 |
| WO | WO 2009/104182 A2 | 8/2009 |
| WO | WO2009097380 A1 | 8/2009 |
| WO | WO2009102792 A2 | 8/2009 |
| WO | WO2009104182 A2 | 8/2009 |
| WO | WO2009113972 A2 | 9/2009 |
| WO | WO2009126781 A1 | 10/2009 |
| WO | 2011/021082 A1 | 2/2011 |
| WO | WO 2011/021082 A1 | 2/2011 |
| WO | WO 2012/112565 | 8/2012 |

OTHER PUBLICATIONS

Extended European Search Report corresponding to EP 13 16 4453.6, completed Jul. 29, 2013 and mailed Aug. 5, 2013; (7 pp).

* cited by examiner

MEANS AND METHOD FOR REVERSIBLY CONNECTING A PATCH TO A PATCH DEPLOYMENT DEVICE

RELATED APPLICATION

The present application claims the benefit of and priority to U.S. provisional patent application Ser. No. 61/302,186, filed Feb. 8, 2010. The content of which is incorporated by reference herein in its entirety.

FIELD OF THE INVENTION

This invention generally relates to a device and method for reversibly coupling a patch to a patch deployment device.

BACKGROUND

An object of the present invention is to provide apparatus and a method for performing corrective surgery on internal wounds such as hernia where invasion of the patient's body tissues is minimized and resultant trauma is reduced.

A hernia is a protrusion of a tissue, structure, or part of an organ through the muscular tissue or the membrane by which it is normally contained. In other words a hernia is a defect in the abdominal wall through which a portion of the intra-abdominal contents can protrude. This often causes discomfort and an unsightly, visible bulge in the abdomen. When such a hernia defect occurs in the abdominal region, conventional corrective surgery has required opening the abdominal cavity by surgical incision through the major abdominal muscles. While this technique provides for effective corrective surgery of the hernia defect, it has the disadvantage of requiring a hospital stay of as much as a week, during which pain is frequently intense, and it requires an extended period of recuperation. After the conventional surgery patients frequently cannot return to a full range of activity and work schedule for a month or more. Accordingly, medical science has sought alternative techniques that are less traumatic to the patient and provide for more rapid recovery.

Laparoscopy is the science of introducing a viewing instrument through a port into a patient's body, typically the abdominal cavity, to view its contents. This technique has been used for diagnostic purposes for more than 75 years. Operative laparoscopy is performed through tiny openings in the abdominal wall called ports. In most surgical techniques several ports, frequently three to six, are used. Through one port is inserted the viewing device, which conventionally comprises a fiber optic rod or bundle having a video camera affixed to the outer end to receive and display images from inside the body. The various surgical instruments are inserted through other ports to do the surgery that normally would be performed through an open incision through the abdominal wall. Because the laparoscopic surgical techniques require only very small holes through the abdominal wall or other portions of the body, a patient undergoing such surgery may frequently leave the hospital within one day after the surgery and resume a full range of normal activities within a few days thereafter.

In repairing hernia the physician needs to first deploy the patch and then to attach the patch to the tissue.

There are many patents and patent applications relating to attaching a prosthesis implant to a tissue via tacks. Each patent and patent application describes a different attachment mechanism via different anchoring means (see for example U.S. Pat. No. 6,447,524). Traditional anchors used in surgery include clips, staples, or sutures, and may also be referred to as tissue anchors. These devices are usually made of a biocompatible material (or are coated with a biocompatible material), so that they can be safely implanted into the body.

Most tissue anchors secure the tissue by impaling it with one or more posts or legs that are bent or crimped to lock the tissue into position. Thus, most traditional anchors are rigid or are inflexibly attached to the tissue. For example PCT no. WO07/021,834 describes an anchor having two curved legs that cross in a single turning direction to form a loop. Those two curved legs are adapted to penetrate tissue in a curved pathway. U.S. Pat. No. 4,485,816 (refers hereinafter as 816') describes surgical staple made of shape memory alloy. The staple is placed in contact of the tissue and then heated. The heating causes the staple to change its shape thus, penetrating the tissue.

U.S. Pat. No. 6,893,452 describes a tissue attachment device that facilitates wound healing by holding soft tissue together under improved distribution of tension and with minimal disruption of the wound interface and its nutrient supplies.

U.S. Pat. No. 6,517,584 describes a hernia patch which includes at least one anchoring device made of shape memory material. The anchoring devices are initially secured to the prosthesis by being interlaced through a web mesh constituting the prosthesis. The attachment is obtained by altering the attachment element's shape from rectilinear to a loop shape due to heat induced shape memory effect.

Yet other patent literature relates to devices for endoscopic application of surgical staples adapted to attach surgical mesh to a body tissue.

An example of such a teaching is to be found in U.S. Pat. No. 5,364,004, U.S. Pat. No. 5,662,662, U.S. Pat. No. 5,634,584, U.S. Pat. No. 5,560,224, U.S. Pat. No. 5,588,581 and in U.S. Pat. No. 5,626,587.

There are a few patent and patent applications teaching the deployment of patches. For example U.S. Pat. No. 5,836,961 which relates to an apparatus used for developing an anatomic space for laparoscopic hernia repair and a patch for use therewith. The apparatus of U.S. Pat. No. 5,836,961 comprises a tubular introducer member having a bore extending therethrough. A tunneling shaft is slidably mounted in the bore and has proximal and distal extremities including a bullet-shaped tip. A rounded tunneling member is mounted on the distal extremity of the tunneling shaft. The apparatus comprises an inflatable balloon. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

More patent literature can be found in PCT no. WO08065653 which relates to a device especially adapted to deploy a patch within a body cavity. The device is an elongate open-bored applicator (EOBP) and comprises (a) at least one inflatable contour-balloon, (b) at least one inflatable dissection balloon. The inflatable contour-balloon and the inflatable dissection balloon are adjustable and located at the distal portion. The EOBP additionally comprises (c) at least one actuating means located at the proximal portion. The actuating means is in communication with the inflatable contour-balloon and the inflatable dissection balloon. The actuating means is adapted to provide the inflatable contour-balloon and the inflatable dissection balloon with independent activation and/or de-activation.

Although all the above described patents and patent applications demonstrate attachment means or deployment means, none of the literature found relates to a reversible connection device which enable a reversible coupling between the patch and the patch deployment device.

Thus, there is still a long felt need for a device that will enable a reversible connection between the patch and the patch deployment device.

SUMMARY OF THE INVENTION

It is one object of the present invention to provide an active reversible connection (ARC) mechanism adapted to provide a reversible attachment between a prosthetic patch and a patch deployment device (PDD); wherein said attachment can be actively revered without requiring any application of force on said patch.

It is another object of the present invention to provide the ARC mechanism as defined above, wherein said ARC mechanism comprising at least one connection clip (CC) 107, hinge-like coupled to said PDD, adapted to attach said patch to said PDD: Said CC is characterized by having at least three configurations: (i) a horizontal configuration in which said CC 107 is substantially horizontal with respect to said PDD 100; (ii) a vertical configuration in which said CC 107 is substantially vertical with respect to said PDD 100; and, (iii) a free motion configuration in which said CC is free to rotate; such that (i) when said CC 107 is in said horizontal configuration said attachment between said patch and said PDD is obtained; (ii) when said CC 107 is in said free motion configuration said detachment between said patch and said PDD is obtained.

It is another object of the present invention to provide the ARC mechanism as defined above, additionally comprising at least one locking bar 203 characterized by at least two configurations: (i) lock configuration in which said lock bar 203 maintains said CC 107 in said horizontal configuration; and, (ii) free configuration in which said locking bar 203 enables said CC 107 a free movement.

It is another object of the present invention to provide the ARC mechanism as defined above, wherein said ARC additionally comprising at least one detachment actuator adapted to reversibly transform said locking bar 203 from said lock configuration to said free configuration.

It is another object of the present invention to provide the ARC mechanism as defined above, wherein said attachment between said patch and said PDD is obtained once said locking bar 203 is in its said lock configuration and said at least one CC 107 is in said horizontal configuration such that the same at least partially penetrates said patch 210.

It is another object of the present invention to provide the ARC mechanism as defined above, wherein said detachment is achieved by transforming said locking bar from said lock configuration to said free configuration via said at least one detachment actuator.

It is another object of the present invention to provide the ARC mechanism as defined above, wherein said detachment actuator comprises a wire 206; further wherein said wire 206 is attached to said lock bar 203.

It is another object of the present invention to provide the ARC mechanism as defined above, wherein said transformation of said CC 107 from said vertical configuration into their said horizontal configuration is performed manually by the physician or by the aid of a dedicated device.

It is another object of the present invention to provide a method for attaching a prosthetic patch to a patch deployment device (PDD). The method comprising steps selected inter alia from:
a. obtaining an active reversible connection (ARC) mechanism adapted to provide a reversible attachment between said prosthetic patch and said PDD; wherein said attachment can be actively revered without requiring any application of force on said patch; said ARC comprising
  i. at least one connection clip (CC) 107, hinge-like coupled to said PDD, adapted to attach said patch to said PDD: Said CC is characterized by having at least three configurations: (i) horizontal configuration in which said CC 107 is substantially horizontal with respect to said PDD 100; (ii) a vertical configuration in which said CC 107 is substantially vertical with respect to said PDD 100; and, (iii) a free motion configuration in which said CC is free to rotate;
  ii. at least one locking bar 203 characterized by at least two configurations: (i) lock configuration in which said lock bar 203 maintains said CC 107 in said horizontal configuration; and, (ii) free configuration in which said locking bar 203 enables said CC 107 a free movement; and,
b. providing said CCs in said vertical configuration;
c. providing said locking bar in said lock configuration;
d. threading said patch through said CC;
e. transforming said CC into its said horizontal configuration thereby providing said attachment between said patch and said PDD;

It is another object of the present invention to provide the method as defined above, additionally comprising step of providing said ARC with at least one detachment actuator.

It is another object of the present invention to provide the method as defined above, additionally comprising step of reversibly transforming said locking bar 203 from said lock configuration to said free configuration via said detachment actuator; thereby enabling free rotation of said CC such that detachment between said patch and said PDD is obtained.

It is another object of the present invention to provide the method as defined above, additionally comprising step of introducing said PDD into a body cavity.

It is another object of the present invention to provide the method as defined above, additionally comprising step detaching said patch from said PDD.

It is another object of the present invention to provide the method as defined above, wherein said detachment additionally comprising steps of reversibly transforming said locking bar 203 from said lock configuration to said free configuration via said detachment actuator; thereby enabling said CC 107 to rotate freely such that said detachment between said patch and said PDD is obtained.

It is another object of the present invention to provide a hernia kit useful in minimal invasive hernia surgery, comprising:
a. a patch;
b. patch deployment device (PDD), adapted to deploy said patch within the abdominal cavity; and,
c. an active reversible connection (ARC) mechanism for reversible attaching said patch to said PDD;
wherein attachment can be actively revered without requiring any application of force on said patch.

It is another object of the present invention to provide the hernia kit as defined above, wherein said ARC mechanism comprising:
a. at least one connection clip (CC) 107, hinge-like coupled to said PDD, adapted to attach said patch to said PDD:

Said CC is characterized by having at least three configurations: (i) horizontal configuration in which said CC 107 is substantially horizontal with respect to said PDD 100; (ii) a vertical configuration in which said CC 107 is substantially vertical with respect to said PDD 100; and, (iii) a free motion configuration in which said CC is free to rotate; such that (i) when said CC 107 is in said horizontal configuration said attachment between said patch and said PDD is obtained; (ii) when said CC 107 is in said free motion configuration said detachment between said patch and said PDD is obtained.

It is another object of the present invention to provide the hernia kit as defined above, additionally comprising at least one locking bar 203 characterized by at least two configurations: (i) lock configuration in which said lock bar 203 maintains said CC 107 in said horizontal configuration; and, (ii) free configuration in which said locking bar 203 enables said CC 107 a free movement.

It is another object of the present invention to provide the hernia kit as defined above, wherein said ARC additionally comprising at least one detachment actuator adapted to reversibly transform said locking bar 203 from said lock configuration to said free configuration.

It is another object of the present invention to provide the hernia kit as defined above, wherein said attachment between said patch and said PDD is obtained once said locking bar 203 is in its said lock configuration and said at least one CC 107 is in said horizontal configuration such that the same at least partially penetrates said patch 210.

It is another object of the present invention to provide the hernia kit as defined above, wherein said detachment is achieved by transforming said locking bar from said lock configuration to said free configuration via said at least one detachment actuator.

It is still an object of the present invention to provide the hernia kit as defined above, wherein said detachment actuator comprises a wire 206; further wherein said wire 206 is attached to said lock bar 203.

It is lastly an object of the present invention to provide the hernia kit as defined above, wherein said transformation of said CC 107 from said vertical configuration into their said horizontal configuration is performed manually by the physician or by the aid of a dedicated device.

BRIEF DESCRIPTION OF THE DRAWINGS

The invention is herein described, by way of example only, with reference to the accompanying drawings, wherein.

DETAIL DESCRIPTION OF THE SPECIFIC EMBODIMENTS

Figure 1A:
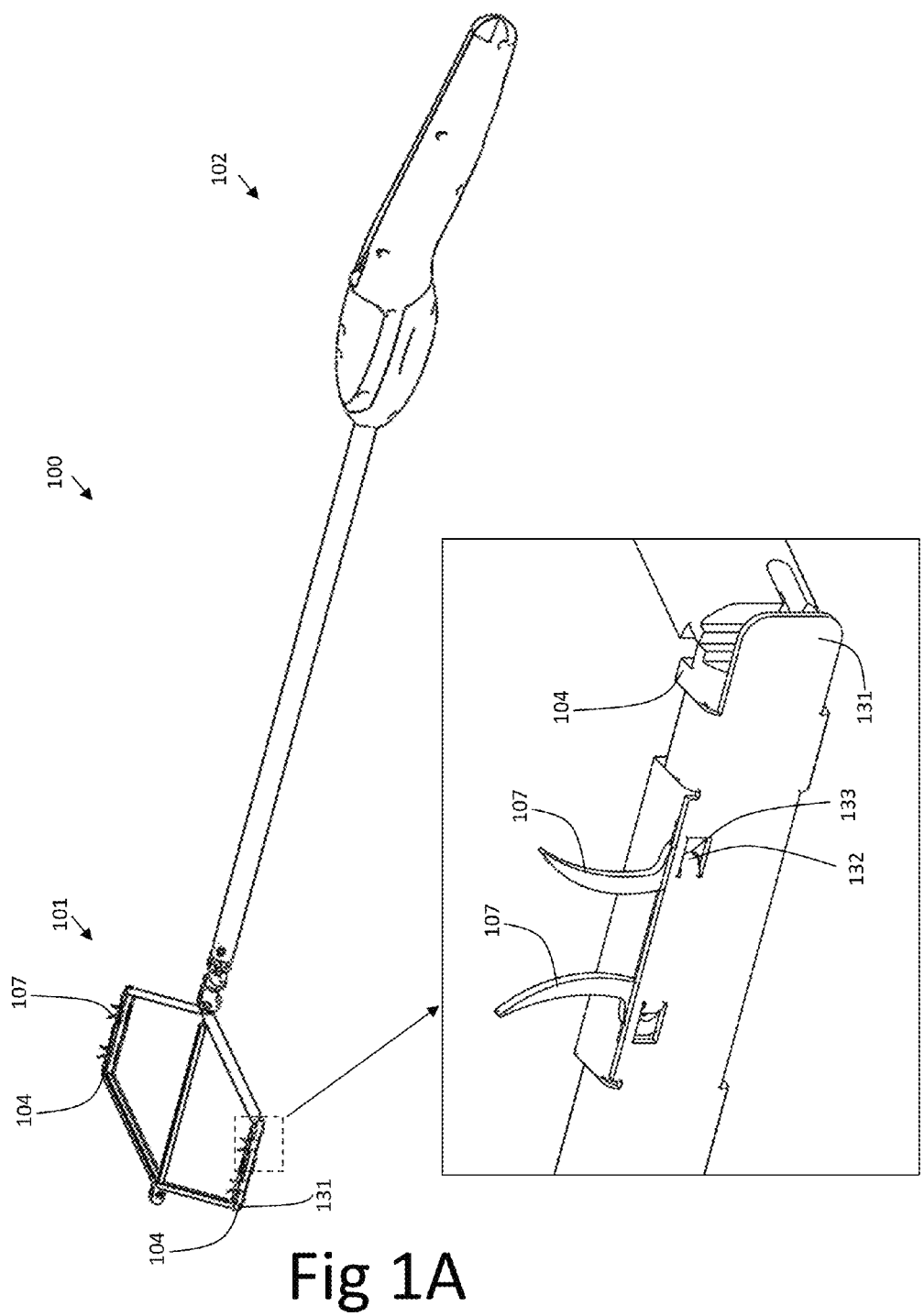
FIG. 1A illustrates an example of a PDD 100 which comprises said ARC mechanism.

The following description is provided, alongside all chapters of the present invention, so as to enable any person skilled in the art to make use of the invention and sets forth the best modes contemplated by the inventor of carrying out this invention. Various modifications, however, is adapted to remain apparent to those skilled in the art, since the generic principles of the present invention have been defined specifically to provides means and method for creating a reversible and active connection between a patch and a patch deployment device.

The present invention provides an active reversible connection mechanism (ARC) between a prosthetic patch and a patch deployment device (PDD) wherein said connection can be performed during a surgery at a standard surgery room by the medical staff.

Furthermore, the present invention provides means so as to enable the surgeon to actively eliminate said attachment once detachment between said PDD and said patch is necessary.

It should be emphasized that some of the major advantages of the present invention, with respect to the prior art, is to provide a fast and intuitive method for creating a reliable connection between a patch and a PDD in the surgery room.

In addition, the present invention provides means to actively disconnect said patch from said PDD, when said disconnection is desired without the need to exert large forces on said patch and/or said tissue.

The term "Hernia" refers hereinafter for umbilical hernia, hiatal hernia, ventral hernia, postoperative hernia, epigastric hernia, spiegelian hernia, inguinal hernia and femoral hernia, generally any abdominal wall related hernia.

The term "hinge" or "hinge-like connection" refers hereinafter as to a type of bearing that connects two solid objects, typically allowing only a limited angle of rotation between them. Two objects connected by an ideal hinge rotate relative to each other about a fixed axis of rotation (the geometrical axis of the hinge). Hinges may be made of flexible material or of moving components.

The term "hinge like connection" can refer to a standard hinge or to a living hinge (i.e., a thin flexible hinge (flexure bearing) made from plastic that joins two rigid parts together while allowing them to bend along the line of the hinge).

The term 'controlled deployment' refers hereinafter to a patch deployment which is continuous; i.e., the deployment is not binary but analogous—there are several deployment levels. This is in contrast so conventional deployment system is now days (see for example U.S. Pat. No. 5,370,650), in which the deployment of the patch relies upon the elasticity of a loop member surrounding the patch such that the patch can be either fully folded or fully unfolded. No intermediate are enabled. In the present invention there can be several deployment stages.

The term 'bidirectional' or 'fully reversible deployment' refers hereinafter to the deployment of the patch, which according to the present invention, is fully reversible. In other words, the patch deployment is bidirectional, i.e., the patch can be fully folded (i.e., deployed within the body) and then, if the surgeon desires, the patch can be fully unfolded simply by the reconfiguration of the flexible arms from the initial stage to the final stage and vice versa.

The term "minimally invasive surgery" refers hereinafter to procedures that avoid open invasive surgery in favor of closed or local surgery with fewer traumas. Furthermore, the term refers to a procedure that is carried out by entering the body through the skin or through a body cavity or anatomical opening, but with the smallest damage possible.

The term "articulation" refers hereinafter to a joint or juncture between two segments of the device. The articulating means of the present invention provides the ability to better adjust the device to the curvature of the treated tissue.

The term "orientation" refers hereinafter to the rotation of the mesh within the abdominal cavity so as to fit to the hernia. Usually the mesh is not symmetric in shape (i.e., rectangular or i.e., ellipse)—therefore it has different directions. By rotating the mesh within the abdominal cavity—one can decide which direction is turned where.

The term "adjusting" refers hereinafter to rolling, folding and winding of the patch, thus preparing and enabling the insertion of said patch into the abdominal cavity.

The term "active reversible connection" refers hereinafter to a coupling between the patch and the patch deployment device PDD in which the coupling/decoupling between the patch and the PDD is enabled by an act performed by the user (namely the physician). Once said User performed said act, said coupling/decoupling is canceled.

According to the present invention the coupling/decoupling is obtained actively via the aid of dedicated connection clips (CC) which are characterized by at least two configurations:

(a) substantially horizontal/parallel configuration (in which an attachment between the patch and the PDD is provided);
(b) substantially vertical configuration; and,
(c) a configuration in which the CCs are free to rotate.

Before explaining the figures, it should be understood that the invention is not limited in its application to the details of construction and the arrangement of the components set forth in the following description or illustrated in the drawings. The invention can be carried out in various ways.

Reference is now being made to FIG. 1A illustrates an example of a PDD 100 which comprises said ARC mechanism.

PDD 100 is defined hereinafter as a surgical device which can introduce a patch into a body cavity of a patient; PDD 100 can deploy said patch such that it is at least partially spared inside the body cavity; alternatively PDD 100 can only introduce said patch into the body cavity without performing any deployment.

In general, PDD 100 comprises at least two portions: a distal portion 101 and a proximal portion 102. The proximal portion is adapted to remain outside the body, adjacently to the user and the distal portion 101 is adapted to be inserted into the body.

The distal portion comprises at least one frame arm (FA) 104 to which the patch is attached. Each FA 104 comprises said ARC mechanism which provide reversible attachment between each FA 104 and the patch 106 such that said patch can be rolled/folded on said distal portion 101, and inserted into the patient's body cavity through a laparoscopic cannula or a small incision.

It should be noted that the term reversible refers hereinafter to the ability to both attach the patch to the PDD and to decouple the same from the PDD.

Said ARC mechanism comprises at least one connection clip (CC) 107. Said CC is coupled to said FA 104 by hinge tab 132. Said ARC is covered by cover 131 which is attached to the FA 104. Cover 131 comprises at least one hinge tab 132 which is adapted to hold said CC 107 attached to FA 104 an to serve as a hinge allowing free rotation of said CC 107. Said hinge tab 132 is inserted through hinge hole 133, located at CC 107 and through hole 134, located at FA 104.

Reference is now being made to FIGS. 2A-2D which illustrate the internal operation of said ARC mechanism. For the purpose of illustration only, cover 131 is removed from these drawings.

A locking bar 203 is located inside groove 204 at FA 104. Said locking bar 203 can move linearly inside said groove 204 and comprises at least one groove 205. Said locking bar 203 is characterized by at least two positions: free position, in which each of said groove/s 205 is substantially located below said CC 107 (see FIGS. 2C and 2D), and lock position, in which said groove 205 is located away from said CC 107 (see FIGS. 2A and 2B).

In the lock position of the locking bar 203, the CC 107 are substantially perpendicular to the FA 104; and in free position of the locking bar 203, the CC 107 are free to rotate (hence, as will be discussed hereinafter a detachment is enabled).

A disconnection wire 206 is attached to said locking bar 203. Said wire 206 can be pulled proximally to the proximal portion 102 and is adapted to transform said locking bar 203 from its said lock position into its said free position.

According to this embodiment, each CC 107 comprises at least 3 sections: protruding portion (PP) 201 adapted to protrude through said patch during said connection process, hinge hole 133, and locking tab 202 which is tilted toward FA 104.

Figure 2A:
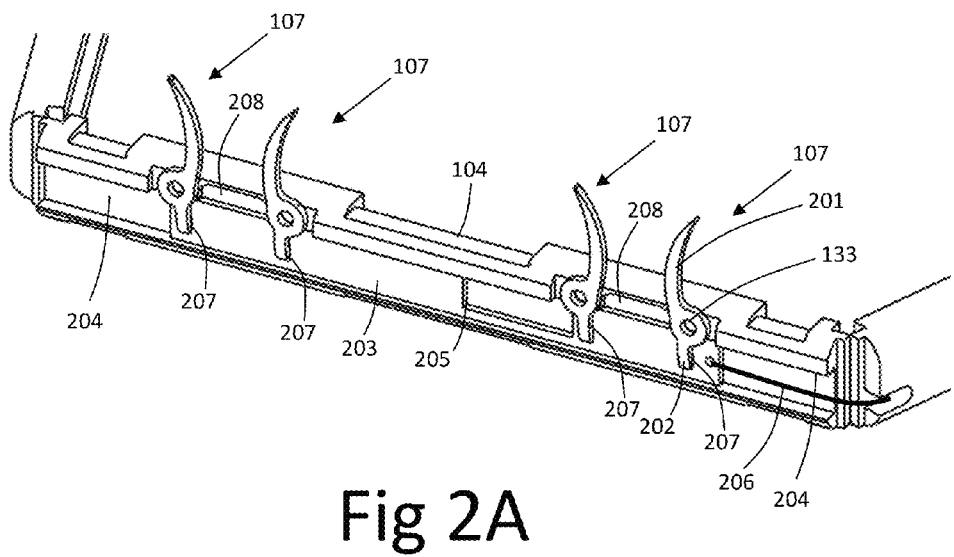
FIGS. 2A-2D illustrate the internal operation of said ARC mechanism.
Figure 2B:
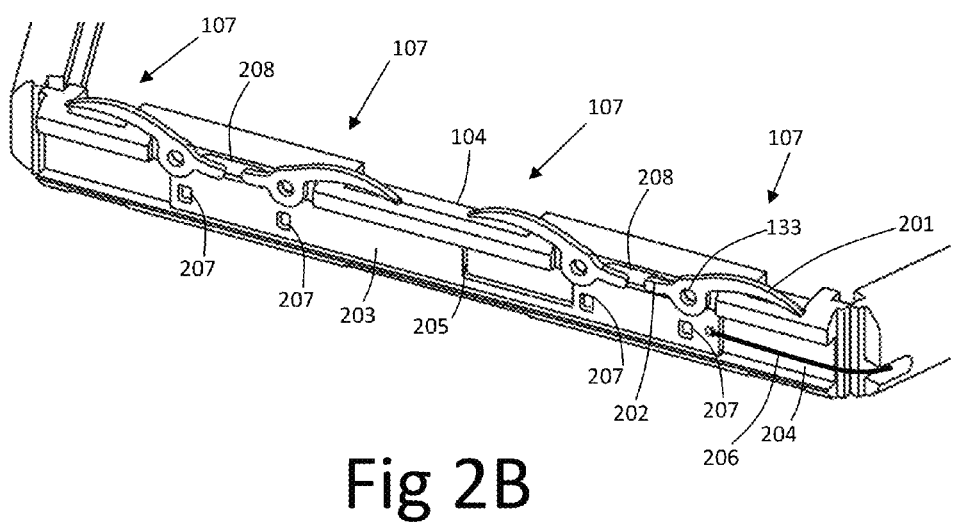
Figure 2C:
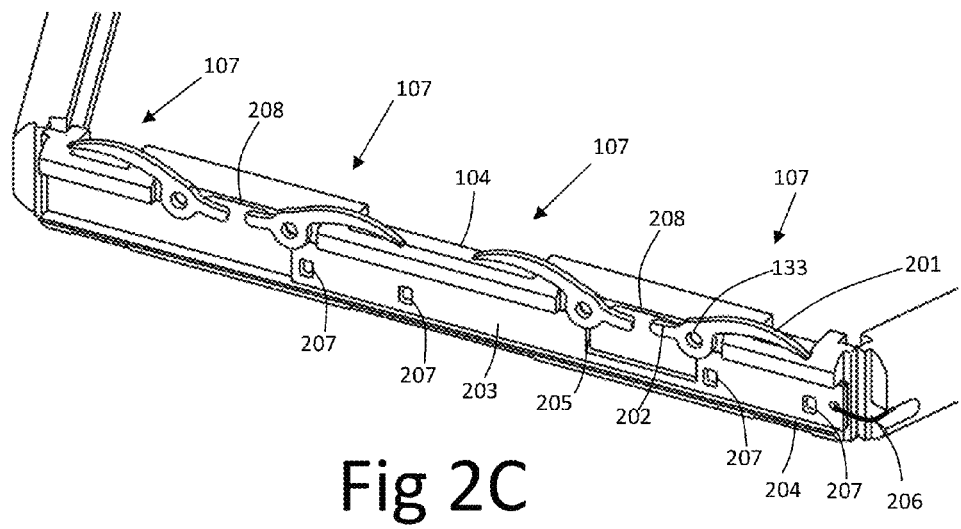
Figure 2D:
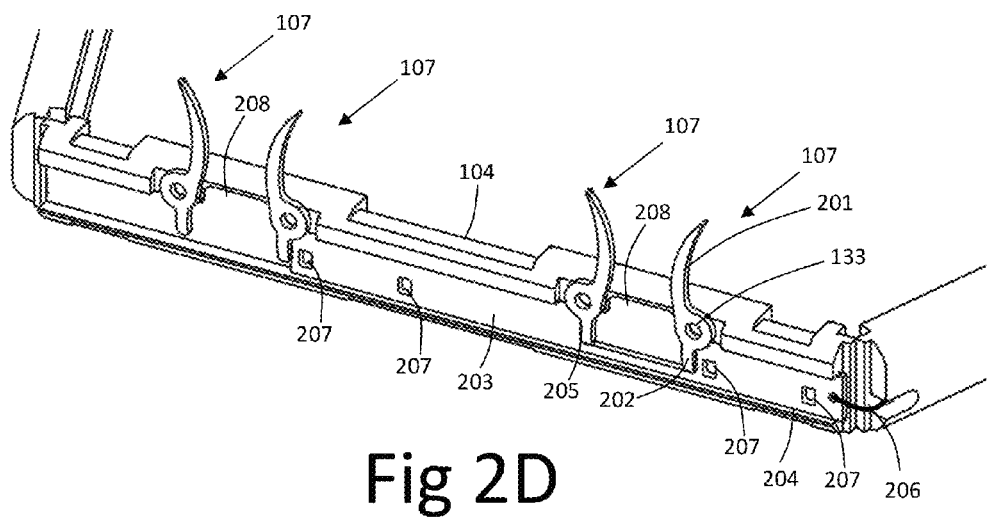

Each of said CC 107 is characterized by at least two configurations: horizontal/parallel configuration in which said CC 107 is substantially horizontal and parallel to said FA 104 (FIGS. 2B, 2C) and vertical configuration in which said CC 107 is substantially vertical with respect to said FA 104 (FIGS. 2A and 2D).

At least one holding hole 207 is located at said locking bar 203 and is adapted to hold said CC 107 in its vertical configuration.

At least one niche 208 in located at FA 104 adapted to accommodate said locking tab 202 of said CC 107 while the last is in its said horizontal/parallel configuration.

Reference is now being made to FIGS. 3A-3D illustrating a method of using said ARC mechanism in order to provide said reversible connection between said patch and said PDD 100. Again, for the purpose of illustration only, cover 131 was removed from these drawings.

Figure 3A:
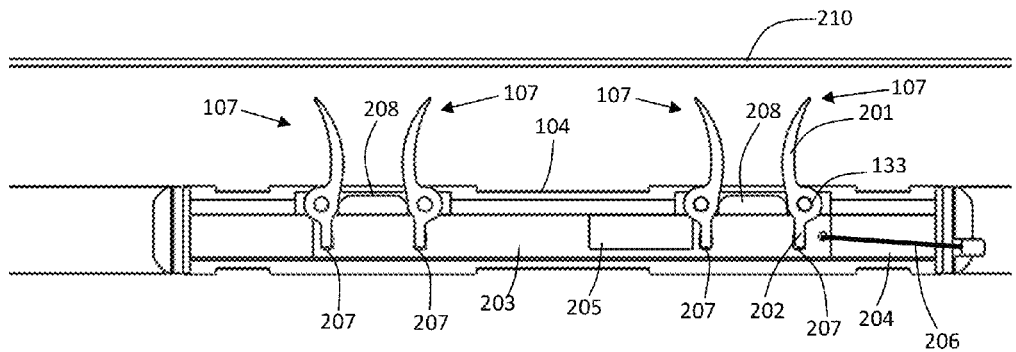
FIGS. 3A-3E illustrate a method of using said ARC mechanism for providing said reversible connection between said patch and said PDD 100.

FIG. 3A illustrates the initial state of said ARC mechanism in which all of said CC 107 are in their vertical configuration and said locking bar 203 is positioned in said lock position.

Figure 3B:
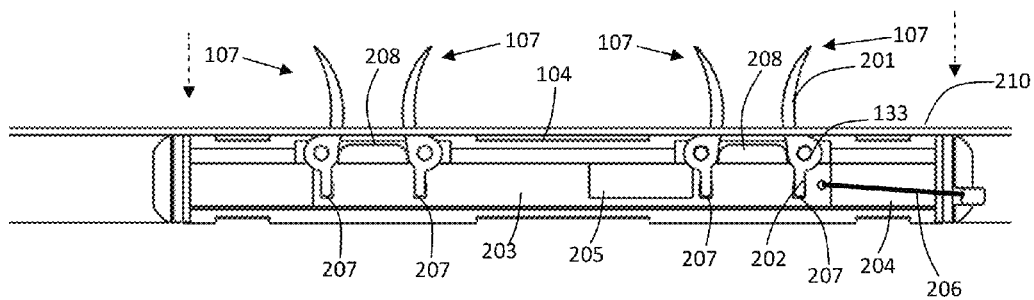

As can be seen in the figure, said locking tab 202 of each said CC 107 is located inside said holding hole 207, therefore each CC 107 is held in its said vertical configuration and can penetrate a patch 210 whilst the last is mounted on top of said PDD (see FIG. 3B).

Figure 3C:
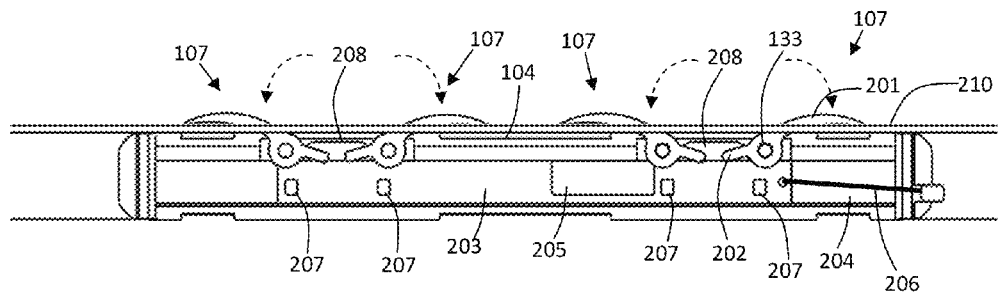

Once said patch is mounted, each of said CC 107 is transformed from said vertical configuration into their said horizontal configuration (see FIG. 3C).

Said transformation can be achieved either manually (i.e., the physician will manually rotate the CCs 107 thereby transform them from said vertical configuration into their said horizontal configuration) or by the aid of a dedicated device.

Once said CC 107 is transformed to its horizontal configuration while said locking bar is in its said lock position, said locking tab 202 is sprigged into niche 208. Since the locking tab 202 is titled inwardly, if said CC 107 is pulled upwardly in this state, the locking tab 202 is stooped by the upper edge of said locking bar 203, therefore, the rotation back to said vertical configuration of said CC 107 is limited by said locking bar 203 and said CCs 107 are locked in said horizontal configuration, holding said patch attached to said FA 104.

It should be pointed out that it is a unidirectional mechanism. In other words, if one tries to force CCs 107 to its vertical configuration, locking tabs 202 will 'bump into' locking bar 203.

Figure 3D:
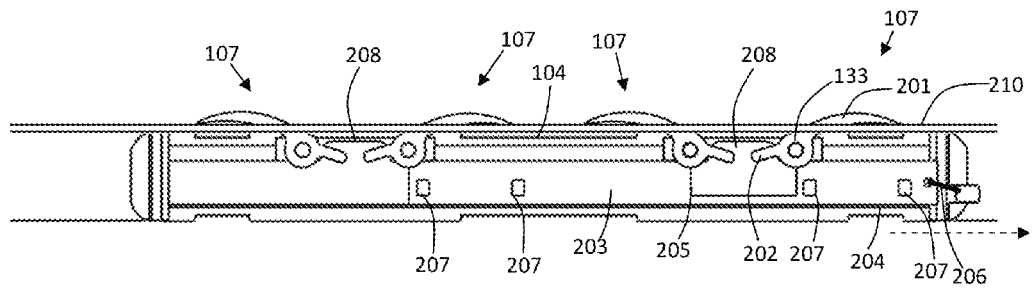
Figure 3E:
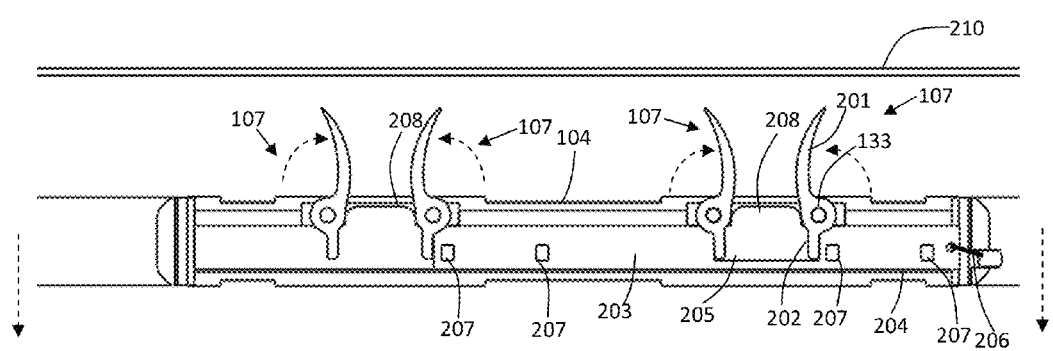

By further pulling said locking bar 203 towards the proximal portion the CCs 107 are unlocked and can be rotated be back to its vertical configuration (see FIGS. 3D and 3E).

Once detachment between said patch 210 and said PDD in desired, locking bar 203 is pulled backward by wire 206, changing the position of said locking bar form its said lock position into its said free position (see FIG. 3D). In said free position of the locking bar 203, the CCs 107 are free to rotate (hence, as will be discussed hereinafter, a detachment between the PDD and the patch is enabled).

Once locking bar 203 is positioned in said free position, said groove/s 205 is located below said CC/s 107, therefore said locking bar 202 is no longer limiting the movement of said CC/s 107 enabling their free movement. In this state, detachment can be obtained by simply pulling said FA 104 away from said patch; as a result, said CC/s 107 rotate back into their said vertical configuration and are released from said patch (see FIG. 2E).

Reference is now made to FIG. 4A-4H, which illustrate an embodiment of a stapling apparatus SA 400 adapted for providing said reversible connection by said ARC mechanism. Said SA 400 comprises a frame 401 which holds the distal portion 101 of a PDD 100. Four staplers 403 are connected to the frame 401 at each cornet by four separate hinges (either standard or living hinges). Each said stapler 403 is adapted to push down the patch 210 through a pair of CC 107 and to transform said CCs 107 from a vertical position into a horizontal position (thus providing said reversible connection). Stapling presses 404 are located at the end of each stapler inside groove 405 and adapted to push CC 107 into horizontal position. Each pair of staplers 403 is connected via bridge 407 in order to prevent lateral movement of said staplers 403 during the stapling process. A snap groove 406 is located at the center of the frame 401 and adapted to reversibly hold said PDD 100 attached to SA 400 until said reversible attachment is obtained.

Figure 4A:
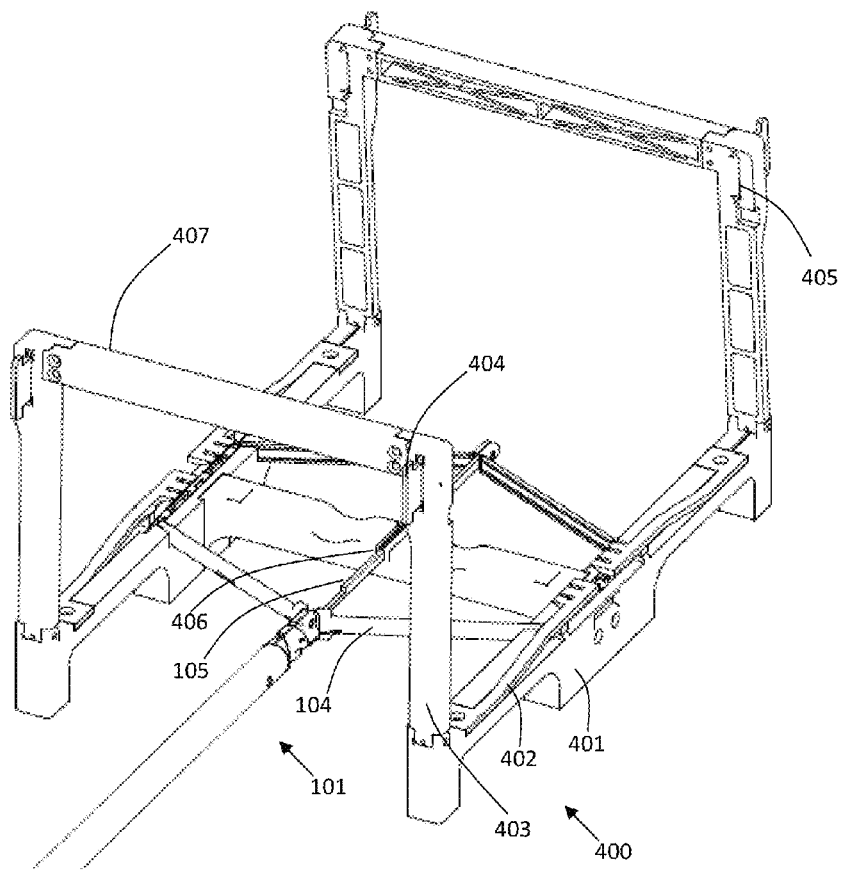
FIG. 4A-4H Illustrate an embodiment of a stapling apparatus SA 400 adapted for providing a reversible connection by the ARC mechanism.
Figure 4B:
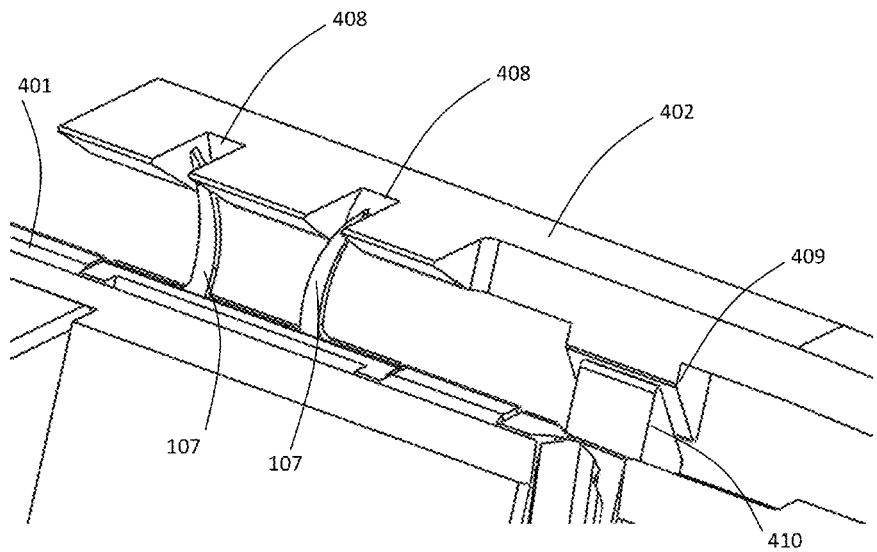
Figure 4C:
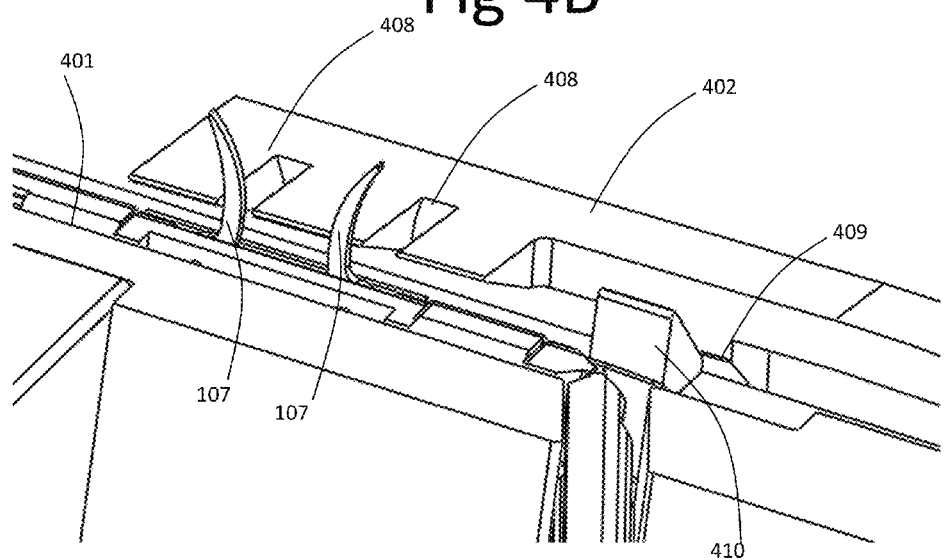
Figure 4D:
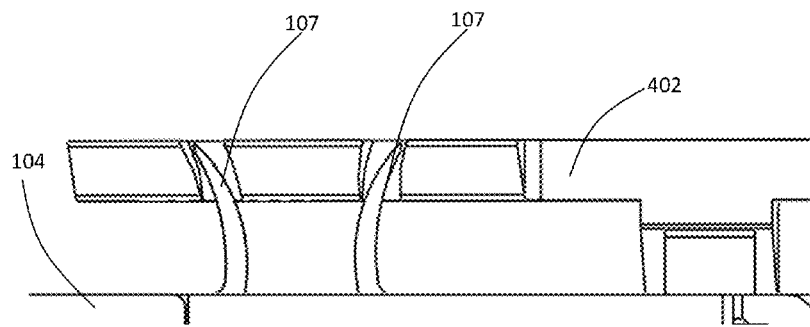
Figure 4E:
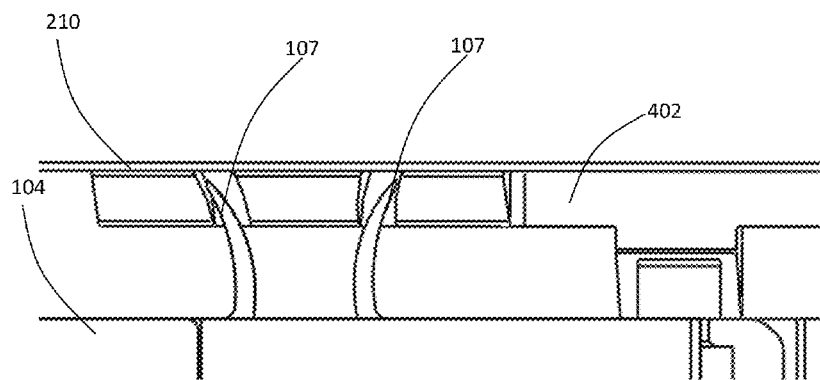

Each pair of CC 107 is held in a vertical position by clip holder (CH) 402. Each said CH 402 is adapted to hold a pair of CC 107 in vertical position in order to allow its insertion through the patch 210 during the stapling process. In addition, CH 402 is adapted the hold the clips vertical during shipment in order to allow stapling in the operation room without the need of any preparation. As illustrated in FIGS. 4B-4C, each CH 402 comprises two grooves 408 which hold the CC 107 in a vertical position. Once stapling process is preformed and the surgeon is lowering the stapler 403 toward the patch, each CH 402 is pushed down and as a result it is also moving laterally. In this state, since the CC 107 are extracted from groves 408, their transformation from vertical into horizontal position is enabled; said lateral movement of said CH 402 is obtained as bulge 409 at CH 402 is sliding along bulge 410 at the stapling frame 401 during the down movement of CH 402.

Figure 4F:
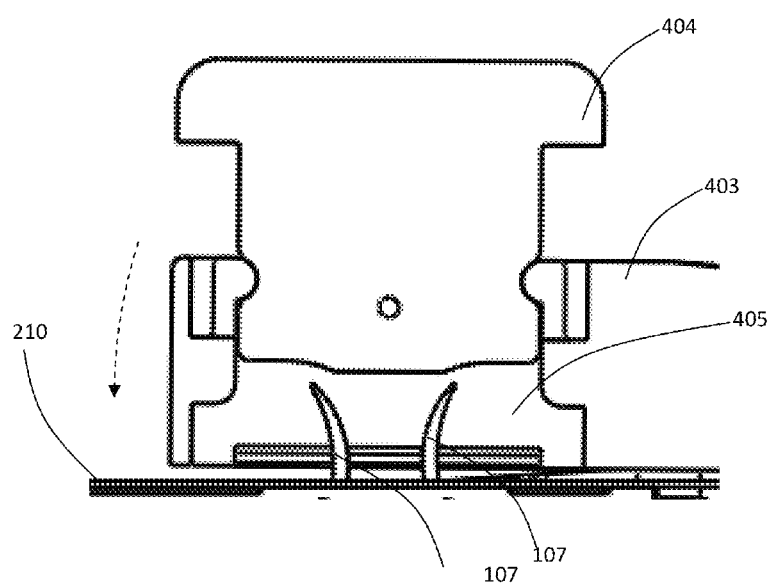
Figure 4G:
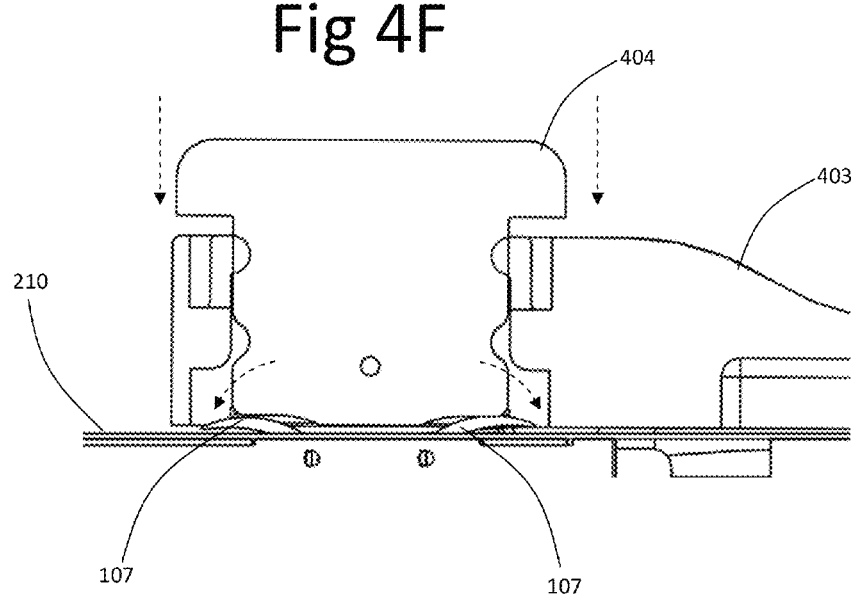

FIGS. 4D-4G illustrate the process of connecting the patch 210 to one pair of CC. At the initial stage (FIG. 4D) the CCs are held vertically by CH 402. Next, a patch 210 is places on top of the stapling apparatus (FIG. 4E); the stapler 403 is then lowered toward the patch 210 by the surgeon (or other member of the medical staff); as a result the two CC 107 are penetrating through patch 210 and into groove 405 (FIG. 4F). During the initial penetration, CC 107 are held by CH 402, thus premature transformation from vertical into horizontal position is prevented. Once the CC 107 are completely inserted into said patch 210, CH 402 is positioned laterally relative to the CC 107 (as also described is FIGS. 4B-4C); at this stage the surgeon push on stapler press 404 and lower it toward CC 107 (FIG. 4G), as a result CC 107 position is transformed form vertical position into horizontal position. Since the said lock bar 203 is located at its said lock position, once CC 107 are substantially horizontal position, they are locked in this stage, thus providing said reversible connection between patch 210 and PDD 100. Once said connection is obtain with all CC 107, PDD is removed from SA 400.

Figure 4H:
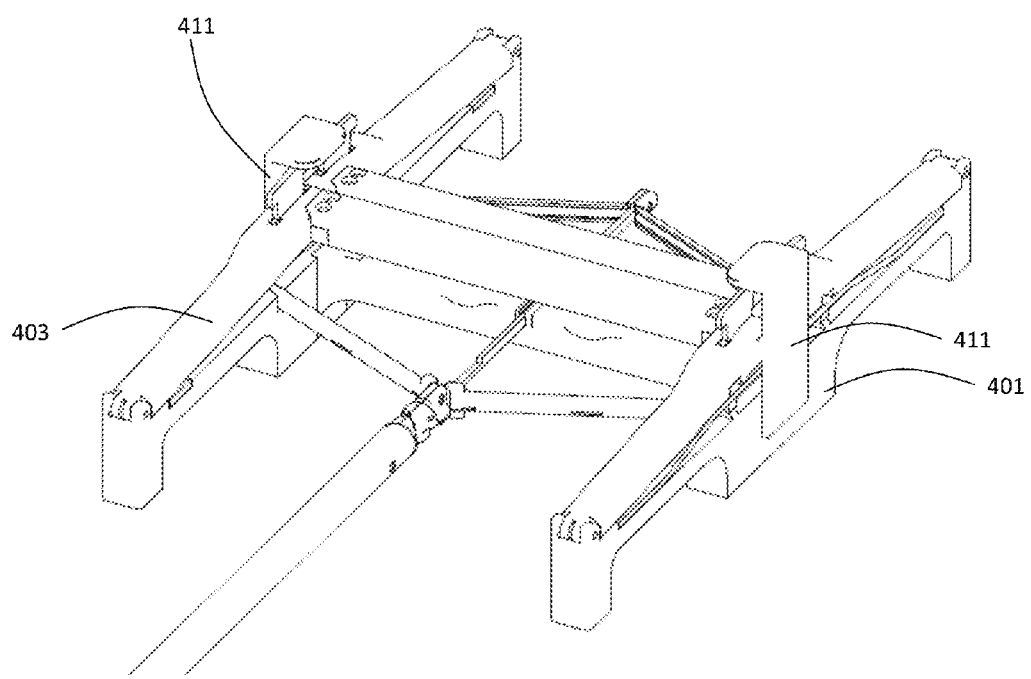

FIG. 4H illustrates the configuration of SA 400 during shipment. In order to reduce package volume during shipment and to keep the device ready for stapling, at least one, preferably two, packaging caps 411 are utilized. Said caps 411 are reversibly attached to the frame 401, and adapted to retain stapler 403 in a substantially horizontal position during device shipment. In addition said caps 411 also prevent down movement of stapler press 404, prevent lateral movement of CH 402 and prevent non-deliberate extraction of PDD 100 from frame 401.

Once the device in removed from its packaging during the surgery, said pack caps 411 are removed by the medical staff in order to allow stapling of the patch 210 to the PDD 100. Once the caps 411 are removed, the staplers 403 springs into horizontal position allowing the placement of patch 210 onto the SA 400 and PDD 100.

In order to allow tight spreading of the patch 210 during surgery, said stapling process is preformed while PDD 100 is not completely opened; as a result, once PDD is completely opened inside the abdominal cavity, it is stretched beyond its original dimension (as was during stapling) therefore tight spreading is obtained.

Figure 5:
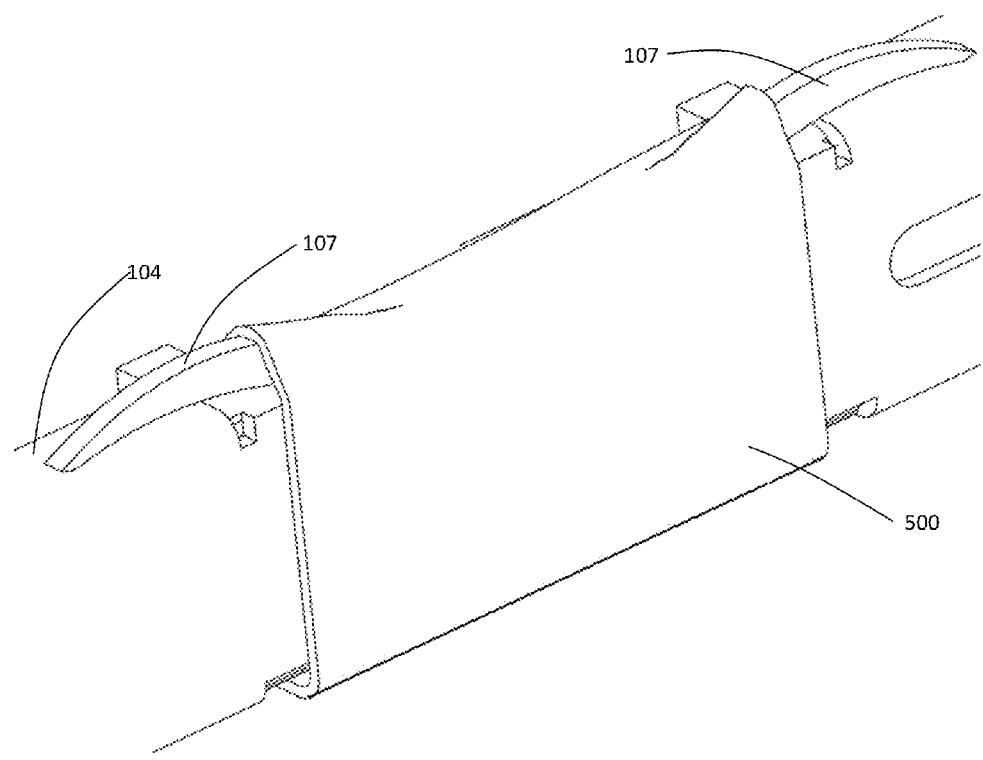
FIG. 5 illustrates an embodiment of a staple return spring SRS 500.

Reference is now being made to FIG. 5 which illustrates an embodiment of a staple return spring SRS 500. In general, SRS is needed in order to return CC 107 into horizontal position immediate after detachment from the patch 210; this is necessary in order prevent damage to internal organs by the sharp tip of CC 107 and in order to prevent CC 107 from being caught at the trocar or at the tissue during device extraction.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A system for closing an aperture in a biological tissue, the system comprising:
   a handle;
   an elongate shah connected to the handle;
   a deployment scaffold connected to the elongate shaft;
   a plurality of attachment members rotatably connected to the deployment scaffold, wherein the plurality of attachment members are configured to releasably retain a surgical implant to a top surface of the deployment scaffold, the plurality of attachment members rotatable relative to the deployment scaffold between a retaining configuration where end portions of the plurality of attachment members configured to pierce the surgical implant are spaced from the top surface of the deployment scaffold at a first distance and a releasing configuration where the end portions of the plurality of attachment members are spaced from the top surface of the deployment scaffold at a second distance that is greater than the first distance; and a locking mechanism that is operably linked with each of the plurality of attachment members, wherein the locking mechanism is adapted to reversibly lock the plurality of attachment members, wherein when the locking mechanism is in a locked configuration, the plurality of attachment members are held in the retaining configuration and when the locking mechanism is in an unlocked configuration, the plurality of attachment members are rotatable to the releasing configuration.

2. The system according to claim 1, wherein the deployment scaffold comprises: a plurality of arms that are configured to move from a retained position to at least one deployed position, wherein the plurality of attachment members are connected to the plurality of arms.

3. The system according to claim 2, wherein the plurality of arms are flexible.

4. The system according to claim 2, wherein the plurality of arms are rigid.

5. The system according to claim 2, wherein the number of the plurality of attachment members is independent of the number of arms.

6. The system according to claim 1, wherein the deployment scaffold comprises:
 a frame; and
 a plurality of deployment arms hingedly connected to the frame, wherein the frame is configured to move from a retained position to at least one deployed position, and the plurality of attachment members are connected to the arms.

7. The system according to claim 1, wherein the deployment scaffold is configured to allow for deployment of the surgical implant and retraction of the surgical implant while the surgical implant is within a patient's body.

8. The system according to claim 1, wherein the deployment scaffold is configured to allow for a plurality of deployment positions.

9. The system according to claim 1, wherein the deployment scaffold comprises an articulating member that allows for adjustment of a position and an orientation of the surgical implant relative to the aperture in the biological tissue.

10. The system according to claim 9, wherein the articulating member allows for vertical flexibility of the deployment scaffold in order to press the surgical implant against the biological tissue.

11. The system according to claim 1, wherein the surgical implant is connected to the system in an operating room.

12. The system according to claim 1, wherein the surgical implant is a patch.

13. The system according to claim 12, wherein the patch is comprised of surgical mesh.

14. The system according to claim 1, wherein the elongate shaft is flexible.

15. The system according to claim 1, wherein the elongate shaft is rigid.

16. The system according to claim 1, wherein the aperture in the biological tissue is an aperture in an abdominal wall.

17. The system according to claim 1, wherein deployment is accomplished by linear movement of the elongate shaft with respect to the handle.

18. The system according to claim 1, further comprising a return mechanism that assists in transforming the plurality of attachment members to the retaining configuration once the surgical implant is detached from the system.

\* \* \* \* \*